United States Patent
Zhang

(10) Patent No.: US 8,193,291 B2
(45) Date of Patent: Jun. 5, 2012

(54) SOLUTION OF METAL-POLYMER CHELATE(S) AND APPLICATIONS THEREOF

(76) Inventor: Caiteng Zhang, Taipei (TW)

( * ) Notice: Subject to any disclaimer, the term of this patent is extended or adjusted under 35 U.S.C. 154(b) by 133 days.

(21) Appl. No.: 10/590,637

(22) PCT Filed: Jan. 31, 2005

(86) PCT No.: PCT/CN2005/000132
§ 371 (c)(1),
(2), (4) Date: Aug. 23, 2006

(87) PCT Pub. No.: WO2005/080489
PCT Pub. Date: Sep. 1, 2005

(65) Prior Publication Data
US 2007/0170393 A1    Jul. 26, 2007

(30) Foreign Application Priority Data
Feb. 23, 2004 (CN) .......................... 2004 1 0004572
Dec. 19, 2004 (CN) .......................... 2004 1 0101965

(51) Int. Cl.
*C08F 251/00* (2006.01)
*C08G 79/00* (2006.01)
*C09K 3/00* (2006.01)
(52) U.S. Cl. ................. 527/300; 252/183.13; 528/395
(58) Field of Classification Search ................. 527/300; 252/183.13; 429/347
See application file for complete search history.

(56) References Cited

U.S. PATENT DOCUMENTS

| | | | | |
|---|---|---|---|---|
| 4,424,346 A | * | 1/1984 | Hall et al. | 536/20 |
| 4,617,244 A | * | 10/1986 | Greene | 429/203 |
| 4,780,518 A | * | 10/1988 | Ceaser | 527/300 |
| 4,921,949 A | * | 5/1990 | Lang et al. | 536/20 |
| 5,059,654 A | * | 10/1991 | Hou et al. | 525/54.1 |
| 5,582,627 A | * | 12/1996 | Yamashita | 71/26 |
| 5,599,916 A | * | 2/1997 | Dutkiewicz et al. | 536/20 |
| 5,912,000 A | * | 6/1999 | Podolski et al. | 424/278.1 |
| 6,589,942 B1 | * | 7/2003 | Ben-Shalom et al. | 514/55 |
| 6,627,099 B2 | * | 9/2003 | Ono et al. | 252/62.2 |
| 7,365,190 B2 | * | 4/2008 | Couture et al. | 536/123.1 |
| 2001/0014334 A1 | * | 8/2001 | Seid et al. | 424/193.1 |

(Continued)

FOREIGN PATENT DOCUMENTS
CN            86104026 A       12/1987
(Continued)

OTHER PUBLICATIONS
Machine translation of KR 2001-0106359.*
(Continued)

*Primary Examiner* — Liam Heincer
(74) *Attorney, Agent, or Firm* — Egbert Law Offices PLLC

(57) ABSTRACT

In a solution of metal-polymer (chelate(s) and applications thereof, a metal-polymer chelate is prepared by mixing water and R—COOH soluble carbohydride molecules and/or hydroxyl or hydroxyl amino and/or carboxyl and/or carbohydrate polymers, metal salts and/or ammonia or amines. The solution of metal-polymer chelate(s) is used extensively in different technical areas including oxidation, condensation, degradation, oxidizing condensation, gas detection, artificial imitated chitosan solution, artificial imitated glucosamine, disinfectant, biochemical reaction for fermentation, biological protein and its metabolite purification, metal enzyme biocatalyst, dry activation of protein enzyme, bacteria preservation systems, oil product, plant, semiconductor, nano filtration, nano material production, nano inorganic matter, nano ceramic, nano plastic, nano textile, battery, liquid crystal, and biochip. These reactions give effects for chemical engineering, gas removal, and waste solvent treatment.

31 Claims, 5 Drawing Sheets

U.S. PATENT DOCUMENTS

| | | | |
|---|---|---|---|
| 2002/0031561 A1* | 3/2002 | Diaz et al. | 424/750 |
| 2002/0143172 A1* | 10/2002 | Ookawa et al. | 536/56 |
| 2003/0054949 A1* | 3/2003 | Chang et al. | 502/159 |
| 2003/0055003 A1* | 3/2003 | Bar-Or et al. | 514/18 |
| 2003/0224974 A1* | 12/2003 | Bolotin | 514/6 |
| 2004/0215045 A1* | 10/2004 | Herrera et al. | 585/818 |
| 2005/0115890 A1* | 6/2005 | Demmer et al. | 210/502.1 |
| 2005/0182021 A1* | 8/2005 | Nichols et al. | 514/54 |
| 2005/0227290 A1* | 10/2005 | Lippard et al. | 435/7.1 |
| 2006/0151396 A1* | 7/2006 | Ren et al. | 210/684 |

FOREIGN PATENT DOCUMENTS

| | | |
|---|---|---|
| CN | 1081930 A | 2/1994 |
| CN | 1234367 A | 11/1999 |
| CN | 1378007 A | 11/2002 |
| CN | 1458072 A | 11/2003 |
| KR | 2001-0106359 A * | 11/2001 |

OTHER PUBLICATIONS

Zhou Ya Guang, The Research on Structure and Property of Chitosan Linking Membrane, Journal of Molecular Science, Sep. 1997, pp. 168-169, vol. 13, No. 3.

* cited by examiner

SOLUTION OF METAL-POLYMER CHELATE(S) AND APPLICATIONS THEREOF

This application is for entry into the U.S. National Phase under §371 for International Application No. PCT/CN2005/000132 having an international filing date of Jan. 31, 2005 and claiming priority to Chinese Applications Nos. 200410004572.3 filed Feb. 23, 2004 and 200410101965.6 filed Dec. 19, 2004, and from which priority is claimed under all applicable sections of Title 35 of the United States Code including but not limited to, Sections 120, 363 and 365(c).

BACKGROUND OF THE INVENTION

1. Field of the Invention

The present invention relates to a solution of metal-polymer chelate(s) and applications thereof, and more particularly to a solution of metal-polymer chelate(s) and applications thereof for a condensation solution, an oxidizing condensation solution and other reacting solutions, and the solution of metal-polymer chelate(s) is used for various applications and chemical engineering areas such as catalyses, gas detections, artificial imitated chitosan solutions, artificial imitated glucosamines, disinfectants, biochemical reactions for fermentation, biological proteins and their metabolite purification, metal enzyme biocatalysts, dry activation for protein enzyme, genetic engineering, bacteria preservation systems, cell or bacteria or protein enzyme culture medium, medical treatments, oil products, plants, semiconductors, nano filtration, nano material production, nano inorganic matters, nano ceramics, nano plastics, nano textiles, batteries, liquid crystals, and biochips, so as to remove organic solvent gases and other gases as well as processing solvent solutions.

2. Description of the Related Art

In general, a condensation is an important process for chemical engineering, and it is commonly known that a styrene gas can be changed into polystyrene solid, and a monomer can be changed into a solid polymer, and these changes are made by condensation and polymerization. However, a polymerization sometimes needs an initialization (such as a partial oxidation) to obtain a successful reaction. In early stages, the structure of a condensation catalyst is very complicated, and an initialization (or a partial oxidation) and a condensation are indispensable to each other. Unlike the present oxidation and condensation that can be held at the same time, a stable gas requires an oxidation and a condensation for the reactions, and some gases even require high temperature and pressure for the reactions, and thus the investments, costs, financial resources and material resources are obviously huge. The present invention comes with a very simple structure and also requires a catalyst and a carrier with the function of performing condensations, oxidizing condensations and other reactions to process organic solvent gases and other gases. In early days, there were carriers for absorbing and neutralizing gases, but there was no carrier to deal with a solvent gas directly, and the reacting carriers at early days came with a very short life. However, the physiologically active life of the present hydroxypropylmethyl celluloses (HPMC) and other matters with special functional groups can be extended unlimitedly and developed to be an artificial imitated chitosan solution containing metal ions, so as to provide high-efficiency, high-density, high-activation and long-life biological carriers. The solution of metal-polymer chelate(s) is used for gas detections and the solution also becomes a metal enzyme biocatalyst.

The solution of metal-polymer chelate(s) can be developed further to provide novel biochemical enzyme systems and enzyme immobilization systems. The immobilization and preservation of bacteria rely on nitrogen gas for the preservation for a long time. The related cultivation and purification are not easy at all and always get contaminated easily, and thus it is necessary to change the carrier after a specific period of time. The concentration of bacteria cannot reach a high level, and thus the potency is very limited. When bacteria are cultivated, the metabolism issue of the nutrition sources is generally taken into consideration, but the chitosan solution or chitosan or humic acid immitated by the hydroxypropylmethyl cellulose (HPMC) at a specific combination does not need to consider the metabolism issue of the nutrition sources anymore. The solution of metal-polymer chelate(s) is used to replace the conventional culture medium with a powerful cultivation of bacteria, enzymes, nucleic acids and cells and also used to develop biological proteins and purifying its metabolite. In the nano technology, a metal solution usually comes with a size of $10^{-6}$ m, and will achieve a nanometer ($10^{-9}$ meter) scale after the solution is dried. The nano scale can be achieved generally by going through a sol-gel method to convert the metal solution into an organic metal, and the chemical process is very complicated. However, the present new enzyme system can provide nano applications for nano filtrations, nano ceramics, nano plastics and nano textiles. The process for the waste solvent treatment is the same, and thus a quick room-temperature condensation and oxidizing condensation can be achieved, and the previous infeasible waste solvent treatment is made feasible now.

In view of the shortcomings of the prior art, the inventor of the present invention based on years of experience to conduct extensively researches and experiments, and finally developed a solution of metal-polymer chelate(s) and applications thereof, in hope of providing a long needed solution for related problems.

As we know, a hydroxypropylmethyl cellulose (HPMC) exists in many plants, and the cellulose in a wood is a natural fiber polymer. In the nature, the physiological activity of the HPMC has functional properties, and the HPMC is nontoxic to human body and free of stimulations or allergic reactions, and thus the HPMC has a very good biocompatibility with human body without producing any antibody. The HPMC used in the chemical engineering area can dissolve heavy metals and different monovalent, bivalent, or trivalent metal ions, in addition to its common usage as a connecting agent or an additive. In fact, an appropriate proportion of monovalent, bivalent, or trivalent metal ions and amino groups can maximize the reaction of oxidized, degradated, condensed and polymerized organic solvents for some specific chemical gases, and the HPMC can be applied in the areas of biological semiconductors, chips and liquid crystals. We usually think that it is necessary for chitosan to use another medium (such as carbon tetrachloride or sodium sulfate) for the condensation, or the reaction must be taken place for the reactions of producing acidic or alkaline gases only, but we may not know that oxygen cations can be produced continuously by air friction, and an oxidized solution with a precise control on its dosage, after the oxidized solution is dried.

In view of the existing shortcomings of the prior art, the inventor of the present invention based on years of experience and professional knowledge to conduct extensively researches and experiments, and finally invented a solution of metal-polymer chelate(s) and applications thereof, in hope of overcoming the foregoing shortcomings.

SUMMARY OF THE INVENTION

Therefore, it is a primary objective of the present invention to overcome the shortcomings of the prior art by providing a novel solution of metal-polymer chelate(s) that features good oxidation, degradation, condensation, and oxidizing condensation capabilities.

Another objective of the present invention is to provide a solution of metal-polymer chelate(s) that is used extensively in the technical areas of chemical engineering, gas detection, artificial imitated chitosan solution, artificial imitated glucosamine, disinfectant, biochemical reaction for fermentation, biological protein and its metabolite purification, dry metal enzyme biocatalyst for promoting the activity of protein enzymes, genetic engineering, bacteria preservation system, cell or bacteria or protein enzyme culture medium, medical treatment, oil product, plant, semiconductor, nano filtration, nano material production, nano inorganic matter, nano ceramic, nano plastic, nano textile, battery, liquid crystal and biochip. The solution of metal-polymer chelate(s) of the invention also can be used for the reactions in the technical area of chemical engineering to remove gases and process waste solvent solutions.

A further objective of the present invention is to provide a solution of metal-polymer chelate(s) that solves existing technical problems and improves the practicability and economic effect, so that the invention can provide high performance and useful applications for the industry.

To achieve the foregoing objectives, the present invention provides a solution of metal-polymer chelate(s) prepared by mixing water, R—COOH, carbohydrate molecules and/or hydroxyl or hydroxyl amino and/or carboxyl and/or carbohydrate polymers and metal salts, wherein each composite is provided as follows: water: 0.1-99.87; R—COOH: 0.01-40; carbohydrate molecule and/or hydroxyl or hydroxyl amino and/or carboxyl and/or carbohydrate polymers: 0.01-30; metal salts: 0.01-30; and the composites are sequentially added and blended, or heated, wherein R—COOH is an organic acid or an organic acid matter.

The following technical measures of the invention are adopted to overcome the technical problems.

In the foregoing solution of metal-polymer chelate(s), the solution of metal-polymer chelate(s) is prepared by using water and R—COOH to dissolve carbohydrate molecules (including glucosamine) and/or hydroxyl or hydroxyl amino and/or carbohydrate polymers (including chitosan) and metal salts and mixing them evenly according to a routine method.

In the foregoing solution of metal-polymer chelate(s), the solution of metal-polymer chelate(s) is prepared by using water and R—COOH to dissolve carbohydrate molecules and/or hydroxyl and/or carbohydrate polymers, and then adding metal salts and ammonia or amine matter, and mixing them evenly according to a routine method.

In the foregoing solution of metal-polymer chelate(s), the solution of metal-polymer chelate(s) is prepared by using water and R—COOH to dissolve carbohydrate molecules and/or monosaccharide bimolecules, and then adding metal salts and ammonia or amine matter, and mixing them evenly according to a routine method.

In the foregoing solution of metal-polymer chelate(s), the solution of metal-polymer chelate(s) is prepared by using water and R—COOH and/or alkaline saponification to dissolve R—COOH carboxylic acid with mid to high quantity of alkyl R such as fatty acid and/or carbohydrate molecules, and then adding metal salts and ammonia or amine matter, and mixing them evenly according to a routine method.

In the foregoing solution of metal-polymer chelate(s), the metal salt is one or more monovalent, bivalent, or trivalent metal salts and has a composition in percentage by mass equal to 0.01~30% of the mass of solution of metal-polymer chelate(s).

In the foregoing solution of metal-polymer chelate(s), the metal salt is a beryllium, magnesium, calcium, strontium, barium, radium, nickel, chromium, lead, copper, iron, zinc, titanium, manganese, cobalt, silver, gold, platinum, palladium, cadmium, lithium, rubidium, cesium, mercury, tin, zirconium, aluminum, thallium, antimony, bismuth, germanium, gallium, molybdenum, tungsten, yttrium, scandium, iridium, rhodium, technetium, osmium, ruthenium, rhenium, vanadium, indium, manganese, lanthandide or actinium series metal salt.

In the foregoing solution of metal-polymer chelate(s), there is one or more R—COOH groups having an amount of 0.01%~40% of the total amount of the solution of metal-polymer chelate(s), wherein R stands for an alkyl radical or an alkyl matter.

In the foregoing solution of metal-polymer chelate(s), the R—COOH is monocarboxylic acid, dicarboxylic acid, tricarboxylic acid, acetic acid, citric acid, vitamin C, salicylic acid, ethylene glycol, formic acid, propionic acid, malonic acid, lactic acid, malic acid, succinic acid, maleic acid, fumaric acid, ortho acid, oxalic acid, lauric acid, adipic acid, tartaric acid, lycium acid, humic acid, nitrified humic acid, fatty acid, an opine of a plant, carboxyl acid fiber, or carboxyl resin such as amberlite IRC-50.

In the foregoing solution of metal-polymer chelate(s), there is one or more carbohydrate molecules and/or hydroxyl or hydroxyl amino and/or carboxyl and/or carbohydrate polymers with a percentage by mass equal to the mass of the solution of metal-polymer chelate(s), and the carbohydrate molecule and/or hydroxyl or hydroxyl amino and/or carboxyl and/or carbohydrate polymer is sucrose, maltose, lactose, rechalose, bicarbohydrates, monocarbohydrate (including glucosamine); degraded oil; or artificial synthetic chitosan, chitosan; seaweed cell wall (containing calcium without the need of adding a metal salt); cereal of a plant such as an unhusked rice of a plant (already having calcium, and thus it is not necessary to add a metal salt) or monosaccharide bimolecules of cytokinin-O-glucosides. In other words, cytokinin is combined with glucose to produce a substance capable of promoting the cytokiniesis, while it has a substance similar to the kinetin; or it goes with polyvinyl alcohol or polyvinyl alcohol having ammonia (or amine) matter; or it goes with humic acid, nitrified humic acid, peat or nitrified humic acid or humic acid having ammonia (or amine) matter without the need of using acid for dissolution; or 0.1~6% of hydroxypropylmethyl cellulose (HPMC) and 1~4% of chitosan; or 0.1~6% of hydroxypropylmethyl cellulose (HPMC) and 1~4% of artificial synthesized chitosan; or it goes with hydroxypropylmethyl cellulose (HPMC) of ammonia (or amine) matter; or hydroxypropylmethyl cellulose (HPMC); or amino polyvinyl alcohol; or the foregoing hydroxyl or hydroxyl and amino and/or carboxyl and/or carbohydrate polymer or the foregoing polymer and oil or the mixture and sugar.

The foregoing solution of metal-polymer chelate(s) is characterized in that the metal-polymer ehelatechelate is a solution of metal-polymer chelate(s) having monosaccharide molecules (containing glucosamine) or containing monosaccharide bimolecules or disaccharide or hydroxyl or hydroxyl and amino and/or carboxyl and/or carbohydrate polymer, wherein the polymer bridging agent (preferably a monosaccharide or a solution of metal-polymer chelate(s) having monosaccharide bimolecules) and/or inorganic polymer carrier (including inorganic and organic bridge inorganic polymers or nano inorganic polymer and/or a plant fiber (including carboxyl acid fiber or modified carboxyl acid fiber) and/or carboxyl resin such as amberlite IRC-50 and amino resin or inorganic matter such as polylysine or aminosilane, wherein the metal-polymer chelate and/or inorganic polymer carrier and/or plant fiber and/or carboxyl resin and amino resin or inorganic matter can be solid-liquid separated, purified to an amino metal compound or an amino metal polymer or an amino nano metal polymer or an amino nano metal compound or a nano metal polymer or a nano metal compound or an amino biological protein or a pure biological protein.

In the foregoing solution of metal-polymer chelate(s), the solution of metal-polymer chelate(s) includes/excludes a moisture absorbent combined with the hybrid.

In the foregoing solution of metal-polymer chelate(s), the polymer bridging agent or the moisture absorbent combined with the hybrid is polyvinylpyrrolidone (PVP).

The foregoing solution of metal-polymer chelate(s) is characterized in that the solution of metal-polymer chelate(s) includes/excludes a protein enzyme or a bacteria or a cell.

In the foregoing solution of metal-polymer chelate(s), the solution of metal-polymer chelate(s) and/or hydroxyl polymer includes/excludes a silicic acid and/or a nano powder.

The foregoing solution of metal-polymer chelate(s) is characterized in that the solution of metal-polymer chelate(s) applied for the production of a nano material or a nano ceramic or a nano plastic or a nano textile in the industry includes gas, liquid and solid ozone, strong oxygen $O^{-2}$ or $O_2^-$, hydrogen peroxide, nitrogen gas, ammonia and ammonia gas, sulfur and sulfur gas, phosphoric acid, nitric acid, hydrofluoric acid, boric acid, sulfuric acid, carbonic acid, sulfonic acid, hydrochlorous acid, trichloroacetic acid, isophthalic acid, phthalic acid, graphite, carbon black, bone, pearl, enamel, The foregoing solution of metal-polymer chelate(s) is characterized in that the solution of metal-polymer chelate(s) applied for the nano plastic or nano textile includes a plastic or rubber polymer.

The forgoing solution of metal-polymer chelate(s) is characterized in that the plastic or rubber polymer is polyamide, polyimide, polyethylene, polyvinyl chloride, polyaniline, polystyrene, polyphenylenevinylene, acrylonitrile-styrene-butadiene, polyethylene oxide, epoxy resin, bakelite, polycarbonate, polypropylene, polyacrylic ester, polyester, polyurethane, polyolefin, polyvinyl butyral, polysiloxanes, pinene oxide (PNO), rubber, nitrile butadiene rubber (NBR), silicone, polyvinylpyrrolidone or its precursor or its oligomer or the foregoing modification and blending system.

Compared with the prior art, the present invention obviously has the following advantages and benefits to achieve the objectives of the present invention, and the main technical content of the invention is described as follows:

The invention provides a solution of metal-polymer chelate(s) that solves sucrose or maltose or lactose or rechalose or dicarbohydrates or monocarbohydrates;

or degradated oil, or artificial synthesized chitosan, chitosan, seaweed cell wall, cereal of a plant such as unhusked rice or cytokinin-O-glucoside, and related monosaccharide bimolecules;

or polyvinyl alcohol solution together with ammonia (or amine) matter or polyvinyl alcohol;

or peat, nitrified humic acid, humic acid solution together with ammonia (or amine) matter without the need of using acid for dissolution or nitrified humic acid, or humic acid;

or other polymer (chemical substance-OH)$_n$ functional group solution together with ammonia (or amines);

or other polymer (chemical substance-OH)$_n$ functional group solution already having amino groups;

or 1~4% of chitosan mixed with 0.1~6% of hydroxypropylmethyl cellulose (HPMC);

or 1~4% of artificial synthesized chitosan mixed with 0.1~6% of hydroxypropylmethyl cellulose (HPMC);

or hydroxypropylmethyl cellulose (HPMC) together with ammonia (or amine) matter;

or independent hydroxypropylmethyl cellulose (HPMC) (which does not require any amino or ammonia or amine matter, if the HPMC is used as degradating solution);

or the foregoing substance mixed with hydroxyl or amino polymer or/and oil or/and sugar;

with the acid (including —COOH organic and inorganic acids such as carboxyl acid) and water, and then adds acidified or chlorinated or hydroxidated (referring to nitrified sodium humate) or inorganic polymer monovalent, bivalent, or trivalent metal ions (that can mix two or more bivalent metal ions), primarily using bivalent metal ions and other ions can assist the heating or the following method is adopted, and the method includes heating and mixing the matters evenly; or mixing the metal ions with smaller ion radius with other metal ions; or partially ferments a small quantity of iron ions first, and then adds the metal ions that are difficult to combine, such that the fermentation continues for the formation; or adjusts the pH value such that the hybrid can be combined with the structure stably.

The foregoing 1~4% of ammonia (or amine) matter is added, and thus it is not necessary to add an amino group (such as chitosan or a mixture of chitosan), and the matter is mixed evenly, or blended at a high speed to form a condensation solution or an oxidizing condensation solution (partially or separately add acidified or chlorinated or hydroxidated (referring to nitrified sodium humate) or inorganic polymer bivalent iron ions having the capability of oxidizing a gas), and blended sufficiently for the combination, so as to achieve the required stability. Such reacting solution can be sprayed in a liquid form directly for process the gas in an airtight space or nano inorganic polymer substantially being a PVA-SI-M hybrid ceramic structure (described in a later section) acts as a catalyst carrier, and adds 0.1~3% of PVP K-30 to the produced condensation solution or oxidizing condensation solution or other reacting solution and serves as a moisture absorbent without affecting the combination of the hybrid reacting solution and the hybrid. Unlike the individual mixed moisture absorption, the moisture absorption of the hybrid can enter into a liquid phase reaction immediately.

Alternatively, no moisture absorbent is used as illustrated below:

If hydroxyl or amino polymer is a mixture of 1~4% of chitosan and 0.1~6% of hydroxypropylmethyl cellulose (HPMC), or a mixture of 1~4% of artificial synthesized chitosan and 0.1~6% of hydroxypropylmethyl cellulose (HPMC), or a hydroxypropylmethyl cellulose (HPMC) together with a small quantity of ammonia (or amine) matter, or an independent hydroxypropylmethyl cellulose (HPMC), then no moisture absorbent will be needed to blend or mix the mixture evenly, and the solution is covered and soaked onto the ceramic structure, and the soaked ceramic is baked and dried to remove any water. In the relative humidity of over 99% or a dry condition, a ceramic catalyst carrier is produced for providing the capability of removing an organic solvent and other gases, as well as a gas having similar molecular weight or structure of the organic solvent for the volatile organic solvent or petroleum gases that can be condensed and oxidized and condensation. The condensation solution or the oxidizing condensation solution can condense a large quantity of organic solvents and waste solvents by a high-speed blending process at room temperature to condense the organic solvent into a clay solid, so as to develop a solvent processing machine.

The chitosan of the invention refers to chitosan and synthetic chitosan, such as the artificial synthetic products available in the market and made by the extraction from shrimp and crab shells. The major quality index for the raw material of chitosan includes color and luster, water content, dust content, viscosity and solubility, etc, and the quality of the sensitivity of the reaction solution is closely related to the preparation of condensation solution or oxidizing condensation solution. Therefore, the required quality indexes of the raw material of chitosan include 20% of water content, 10% of dust content (or the ratio of thickness to viscosity is 0.5~5.5), and a good solubility. In the condensation or oxidation solution prepared according to this method, the concentration of chitosan is generally 0.1~10%, and the optimized concentration is 1~6%.

A chemical compound having the same chemical conditions and functions as the chitosan includes a hydroxypropylmethyl cellulose (HPMC) and an amino group, and the metal ion acts as a medium for being a catalyst for the metal ions, such that the hydroxypropylmethyl cellulose (HPMC) can be mixed with $NH_3$. If the hydrogen of a R—OH functional group of the hydroxypropylmethyl cellulose (HPMC) is dehydrogenated and dehydrated by the metal such that $NH_2$ an be haifly bridged and combines with the hydroxypropylmethyl cellulose (HPMC) to produce R—$NH_2$. By then, this solution is a polymer hybrid having the same chemical solution, chemical state and chemical molecular structure as those of chitosan, and becomes an artificial imitated chitosan solution containing metal ions. The bacteria or enzyme or nucleic acid or partial cell body is developed to a long-life, high-concentration bacteria or enzyme or nucleic acid or cell body carrier. The imitated chitosan of the artificial imitated chitosan solution can be used in any area that the chitosan is used. The solution is fermented to produce a metal to a nano scale, and nano metal particles or nano metal oxides or nano complex metal oxides can be obtained by gas phase or liquid phase or combustion or carbonization methods. The imitated chitosan is developed into liquid crystal solution and other aspects for the applications in eight major enzyme systems. The principle for these eight major enzyme systems is similar to the principle described above. Regardless of having hydroxyl or hydroxyl and amino and/or carboxyl and/or carbohydrate polymer or disaccharide or monosaccharide or monosaccharide bimolecule, the imitated chitosan can be combined with the metal salts and then combined with carboxyl and amino groups to produce low to mid polymer metal-polymer chelates. Some enzyme systems use inorganic polymer carrier and/or plant fiber and/or carboxyl resin and amino resin or inorganic matter and/or enzyme system and the principle for the application in biochemical and nano areas.

In view of the description above, the present invention provides a hybrid structured polymer, wherein the hydroxypropylmethyl cellulose (HPMC) is soaked in an acidic solution with a concentration of 0.1~10%, and in fact this solution is made according to a formula with the composition of water: acetic acid or other carboxylic acid:hydroxypropylmethyl cellulose (HPMC) or other (chemical substance-OH)$_n$ polymer:acidified or chlorinated monovalent, bivalent, or trivalent metal ions equal to a proportion within 97:1:1:1 and 88:4:4:4, and the composites are added and blended sequentially, and ammonia (or amine matter) is added. Since it already has an amino group, and thus it is not necessary to add the amino group. A bacteria or enzyme or smaller nucleic acid or partial cell body can be added for the fermentation and growth and used for the biochemical area and producing nano and liquid crystal materials.

Compared with the prior art, the foregoing technical solution of the present invention has the following advantages:

1. The present invention provides a quick reaction for the solvent gas or liquid, without requiring a high temperature or a high pressure. The reaction is held simply at room temperature, and thus the invention can save lots of financial resources and material resources, and thus it is cost-effective.

2. The present invention is very safe since it does not require any fire, and there will be no industrial safety issue.

3. The invention provides long expiration time, worn-out resistance and life expectancy, and it is free from saturation due to the catalysis.

4. The invention solves the problem of organic solvent treatment and the difficulty of fermentation, and also overcome the bottlenecks on the oxidation capability, condensation capability, oxidizing condensation capability, and degradation capability of the reaction.

5. The invention creates an artificial imitated chitosan solution containing metal ions to improve the sources and diversified applications of chitosan.

6. The invention creates a new culture medium for gas detection, artificial imitated glucosamine, disinfectant, biochemical reaction for fermentations, biological protein and its metabolite purification, genetic engineering, bacteria preservation system, medical science, oil product, plant, semicondctor applicability and cell multiplication.

7. The invention creates a new technology for producing nano filtrations, nano materials, nano ceramics, nano plastics and nano textiles.

8. The invention provides a very good metal enzyme biocatalyst.

9. The invention creases a new technology for producing batteries, liquid crystal materials and biochips.

BRIEF DESCRIPTION OF THE DRAWINGS

The description above only provides an overview of the technical solution of the present invention, and the objectives, shape, structure, apparatus, characteristics and effects will become apparent by the detail description together with the accompanying drawings as follows.

DETAILED DESCRIPTION OF THE PREFERRED EMBODIMENTS

Figure 1:
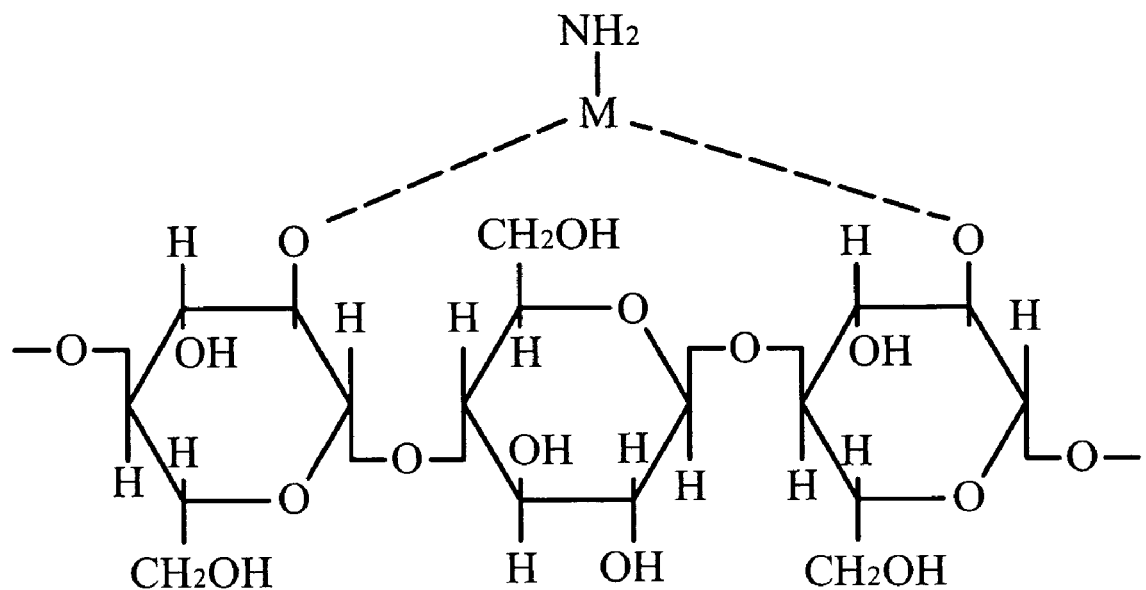
FIG. 1 is a schematic view of the structure of R-M-$NH_2$ used in the present invention, wherein the R-M-$NH_2$ is produced after dehydrating a hydroxyl metal of the hydroxypropylmethyl cellulose (HPMC) and adding an amino group.
Figure 2:
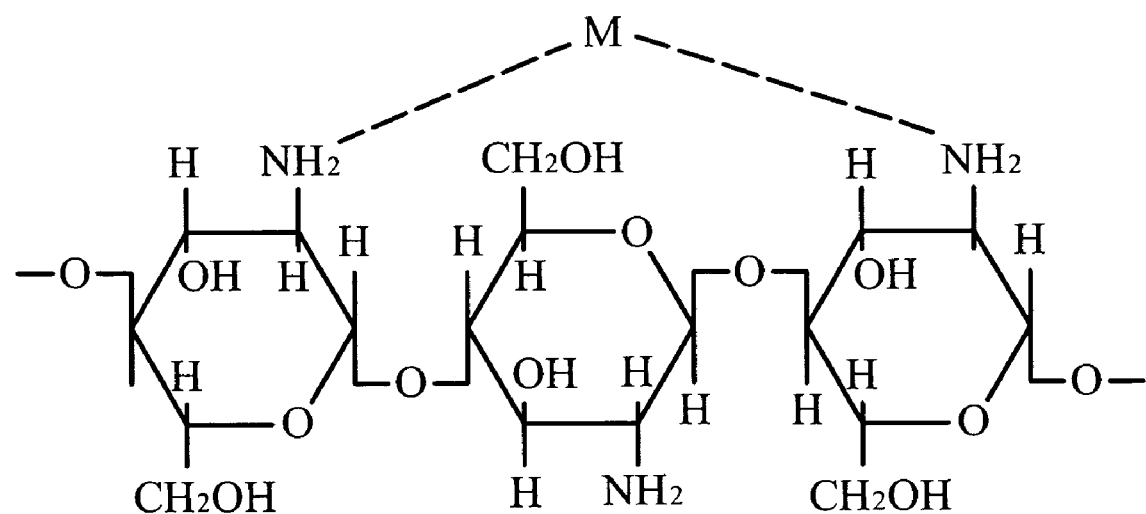
FIG. 2 is a schematic view of the structure of R—$NH_2$-M used in the present invention, wherein the chitosan and metal solution are obtained by a direct reaction.
Figure 3:
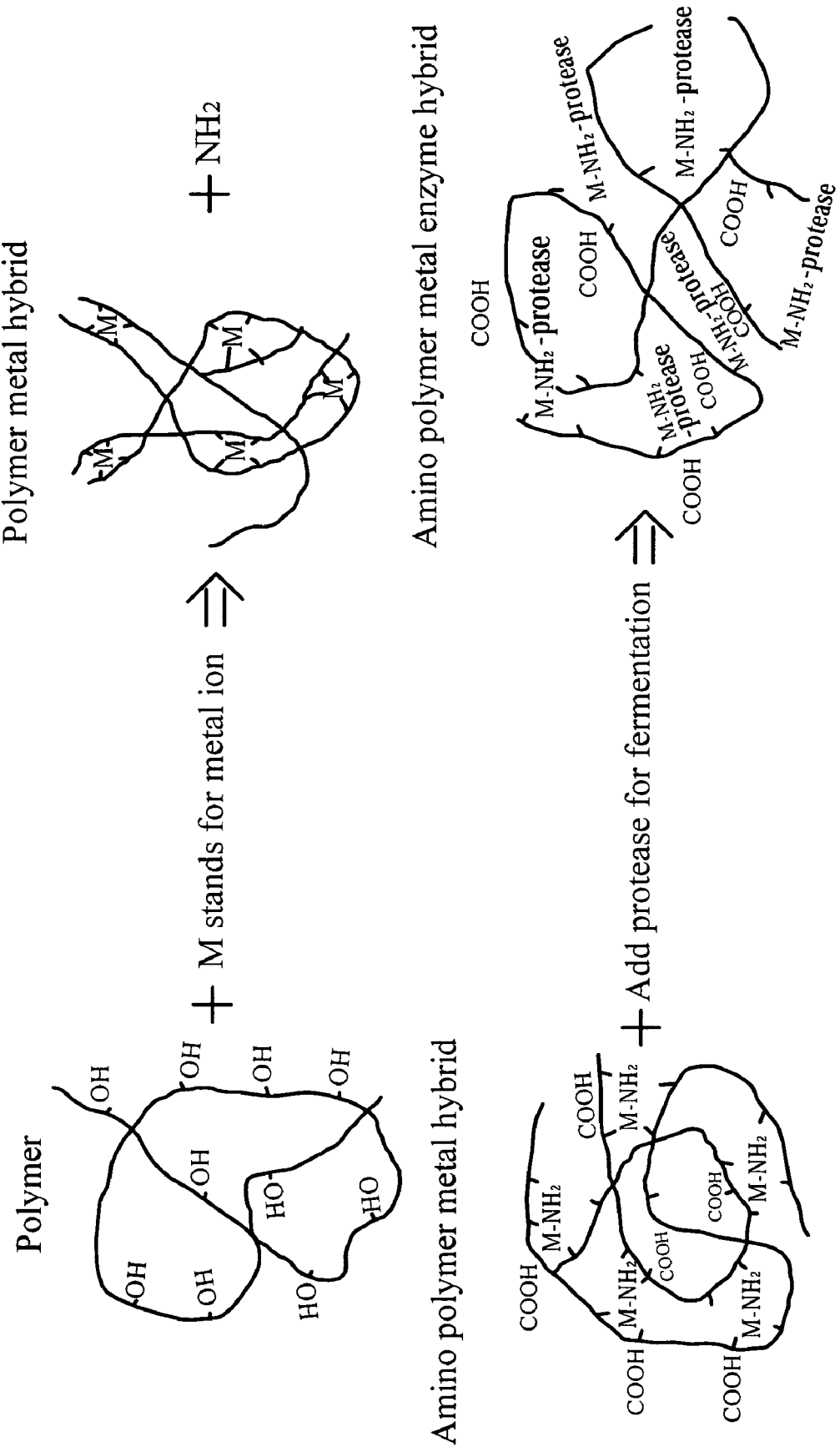
FIG. 3 is a schematic view of the process of producing an amino polymer metal enzyme hybrid of the present invention, by reacting the carbohydrate molecule and/or hydroxyl or hydroxyl amino and/or carboxyl and/or carbohydrate polymers with the metal ions to obtain the polymer metal hybrid, and the polymer metal hybrid further includes an amino group or an amino polymer metal hybrid obtained from the reaction to combine with an amino polymer metal hybrid containing —COOH carboxyl group for the fermentation of protein enzymes to obtain the amino polymer metal enzyme hybrid.
Figure 4:
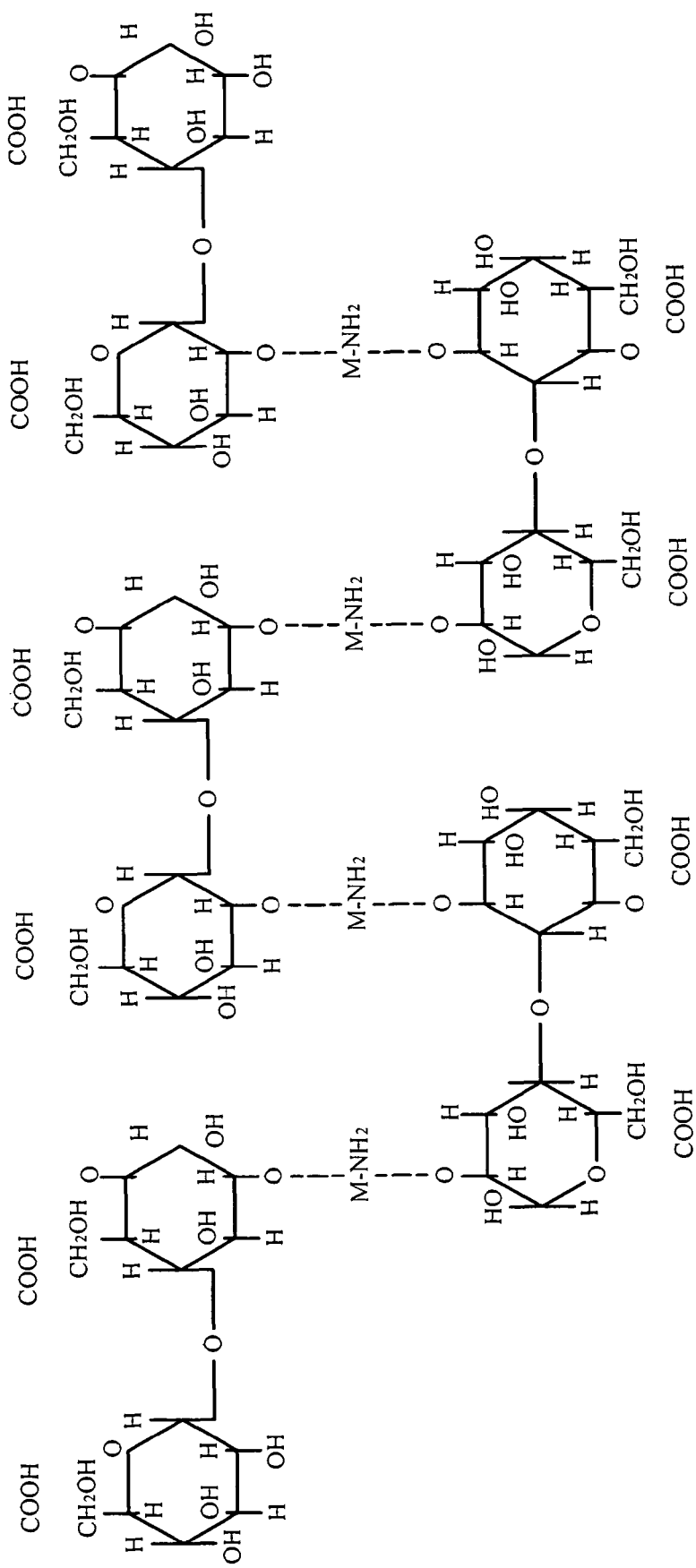
FIG. 4 is a schematic view of a zigzag shaped structure of maltose being added to organic carboxyl acids, metal salts, and amino groups in accordance with the present invention.
Figure 5:
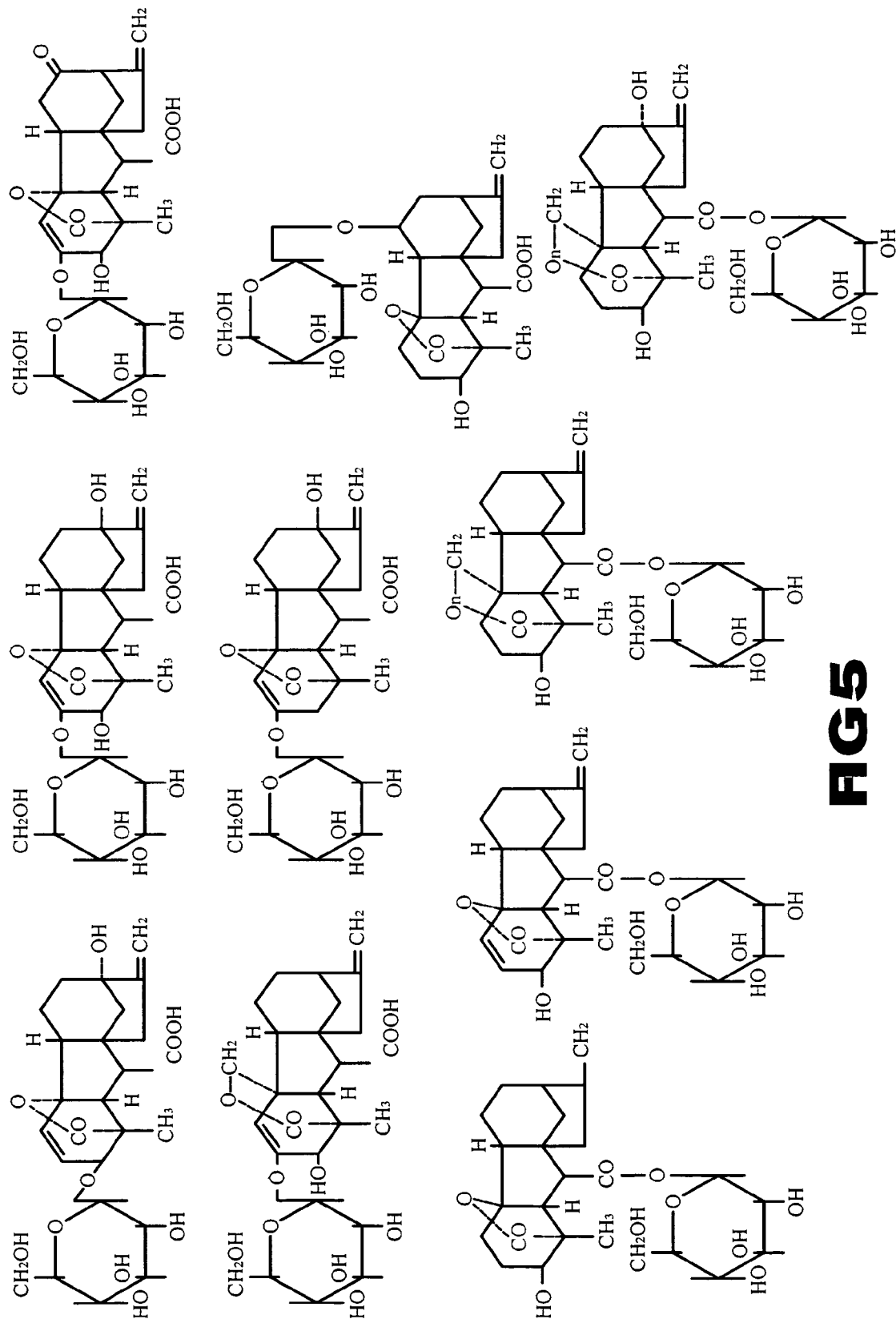
FIG. 5 is a schematic view of a series of structure of a monosaccharide bimolecule without being added to organic carboxyl acids, metal salts or amino groups, such as cytokinins containing monosaccharide bimolecule in a plant in accordance with the present invention.
Figure 6:
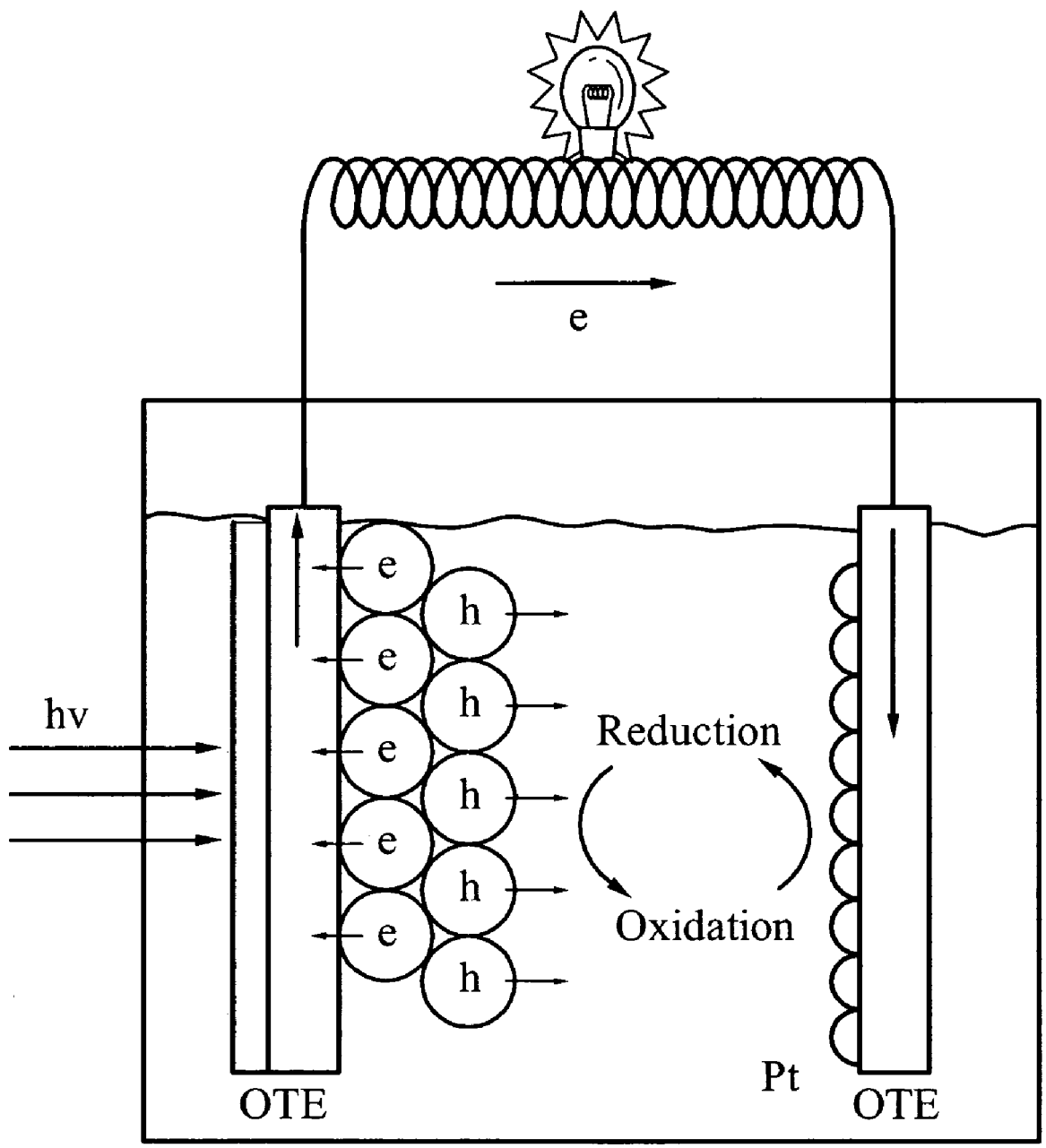
FIG. 6 is a schematic view of a mechanism for producing ultraviolet current in an oxidation semicondctor film of a biofuel battery in accordance with the present invention.

To make it easier for our examiner to understand the objective of the invention, its structure, innovative features, and performance, we use a preferred embodiment together with the attached drawings for the detailed description of the invention.

The present invention provides method for producing a polymer hybrid structured solution, and the method comprises the following steps:

1. Use an acid including 1~10% of acetic acid or other acids (including —COOH carboxyl organic and/or inorganic acid) as a solvent for mixing the solution for a predetermined time at high temperature or room temperature or temperature below room temperature.

2. Prepare a matter including 0.1~10% of sucrose, or maltose, or lactose, or rechalose, or bicarbohydrate, or monocarbohydrate, or degradated oil, or artificial synthesized chitosan, chitosan, or cytokinin-O-glucosides (cytokinins refer to cytokinin combined with glucose and capable of promoting the cytokiniesis while having a physiological action similar to the kinetin) including monosaccharide bimolecule, or a polyvinyl alcohol solution together with ammonia (or amine) matter or polyvinyl alcohol, or a nitrified humic acid or a humic acid solution together with ammonia (or amine) matter, without the need of using acid for dissolution or humic acid, or other polymer (chemical substance-OH)$_n$ functional group solution together with ammonia (or amine) matter, or other polymer (chemical substance-OH)$_n$ functional group solution that already has an amino-$NH_2$ group, or a mixture of 1~4% of chitosan and 0.1~6% of hydroxypropylmethyl cellulose (HPMC), or a mixture of 1~4% of artificial synthesized chitosan and 0.1~6% of hydroxypropylmethyl cellulose (HPMC), or a hydroxypropylmethyl cellulose (HPMC) together with ammonia (or amine) matter, or an independent hydroxypropylmethyl cellulose (HPMC) (it is not necessary to have an amino or ammonia or amine matter, if the HPMC is used as a degradation solution), or the foregoing several liquids are mixed.

3. Add 1~4% of acidified or chlorinated or hydroxgenated (referring to nitrified sodium humate) or inorganic polymer monovalent, bivalent, or trivalent metal ions (which can mix two or more kinds of bivalent metal ions); and the bivalent metal ions are used primarily, and other ions are used to assist the heating, or the foregoing method is adopted such as heating and mixing the ions evenly; or the metal ions with a small ion radius must be mixed with other metal ions; or a trace of iron ion is fermented first, and then the metal ions that are difficult to be combined are added, so as to continue the fermentation and formation; or the pH value is adjusted for performing a hybrid combination and stabilizing the structure.

4. Add the foregoing 1~4% of ammonia (or amine) matter, preferrably ammonia water. If ammonia water is not available or cannot be used, then ethylenediamine or other amines can be used instead. Since there is an amino group already (such as chitosan or a mixture of chitosan), therefore it is not necessary to add amino groups. The ammonia or amine matter is mixed evenly or blended at a high speed to form:

a. Condensation solution b. Oxidizing condensation solution:

Partially add (iron ions mixed with other kinds of metal ions) or separately add the foregoing 0.1~3% of metal ions or 0.1~100% of acidified, or chlorinated or hydroxidized (referring to nitrified sodium humate) or nitrified or inorganic polymers with bivalent iron ions that has an oxidizing capability for the gas. Manganese ions can be used as well, which constitutes an oxidized condensation solution.

c. The more the additives in the solution, the more powerful is the oxidizing capability. As a result, the solution becomes an oxidizing solution:

An ideal upper limit is 100%, since chitosan carries positive charges and preferably has amino groups, and the complex metal iron ion (and the iron ion and a mixture of other metal ions) can induce a push or a pull in opposite directions to produce negative electrons when carrying out the oxidization, and the oxidation is held at the reacting gas, so as to produce anions for the oxygen gas and also produces oxygen cations.

If the main body is chitosan or humic acid having complex metal iron at an ion state, the produced carrier no longer needs a moisture absorbent or a very dry sensitivity for the applications.

5. Such condensation solution or oxidizing condensation solution or oxidized reaction solution or degradation reaction solution and a content of 0.1~3% PVP K-30 are melted evenly without affecting the moisture absorbent of the reacting solution of chelate(s), or no moisture absorbent is used as follows:

The main body is made by mixing 1~4% of chitosan mixed with 0.1~6% of hydroxypropylmethyl cellulose (HPMC), or mixing 1~4% of artificial synthesized chitosan with 0.1~6% of hydroxypropylmethyl cellulose (HPMC), or a hydroxypropylmethyl cellulose (HPMC) together with a trace of ammonia (or amine) matter, or an independent hydroxypropylmethyl cellulose (HPMC).

This solution is sufficiently permeated, soaked, covered by a nano inorganic polymer, substantially a PVA-SI-M hybrid (which will be described in details in a later section) in a ceramic structure, so that the ceramic and reacting solution are combined completely and then baked to dry. The attaching force is enhanced by the viscosity of the PVP K-30, and the moisture absorption and deliquescence of the PVP can absorb the moisture of the carrier easily. If the carrier is blown dry and reacted with the solvent gas, the condensation solution has a very high sensitivity for a liquid-phase (including water) reaction, but the reacting sensitivity at a dry state without water will be very poor.

Since chitosan carries a positive charge, the mixed hydroxypropylmethyl cellulose (HPMC) under the force of metal ions tends to absorb the amino group of chitosan, and gives rise to an ionization of electrons, so that the sensitivity can be improved and no moisture is needed. If the main body is artificial synthesized chitosan or chitosan, or a polyvinyl alcohol solution mixed with ammonia (or amine) matter, or a humic acid solution mixed with ammonia (or amines) matter, or a functional group solution of other polymer (chemical substance-OH)$_n$ mixed with ammonia (or amine) matter, or a functional group solution of other polymer (chemical substance-OH)$_n$ already having-$NH_2$ amino group, then it will need moisture, or a dehydrogenation and dehydration of metal ions depending on the situation (if it is a —OH functional group) to cope with the —NH$_2$ functional group and the bridge occurs at the polymer metal hybrid (for organic solvent gas), or other gases or liquids at room temperature can give rise to an oxidizing degradation and condensing polymerization, and thus the next step must rely on the deliquescence and high humidity (including water) of the PVP K-30 or air at a dry state for the operation, so that the reaction of the carrier for removing the organic solvent gas will be very smooth and able to last for several months or even one year without being saturated.

6. It is necessary to add bacteria or enzyme or nucleic acid or cell body carrier in the fermentation for different applications.

The foregoing functional groups in the solution of the PVA or other polymer (chemical substance-OH)n or other polymer (chemical substance-OH)n already having —NH2 amino group, or chitosan, or humic acid, or hydroxypropylmethyl cellulose (HPMC) have the following fermentations (The first three are not for sure, or the fermentation requires a carbohydrate to act as an accelerant, and if its (R—OH)$_n$ is similar to a carbohydrate structure, the solution will be dissolved by the carboxyl group, and there is an amino group allocated in the metal hybrid structure, and the molecular bond includes asymmetric carbon atoms in a special helix form to assure the occurrence of the fermentation) and the following properties similar to the principle of the hybrid including hydroxypropylmethyl cellulose (HPMC) together with metal ions and amino compounds and featuring a high-efficiency and enduring stable fermentation. If metal ions are used as a medium for mixing hydroxypropylmethyl cellulose (HPMC) with NH$_3$. If hydrogen in the R—OH functional group of the hydroxypropylmethyl cellulose (HPMC) is dechlorinated and dehydrated to produce R-M by the metal ions:

a. If the reacting quantity of the metal ions is small and the reacting quantity of the amino groups is relatively large, the hybrid structure will not be tight, so that the ionization of the metal ions is increased greatly, the activity is improved, and the catalytic sensitivity is raised accordingly, and it tends to have the characteristics of an oxidizing condensation.

b. If the reacting quantity of the metal ions is relatively large, and the reacting quantity of the amino groups is relatively high, then the hybrid structure will be tight, and a condensation will be conducted.

c. If the reacting quantity of the metal ions is too large and the reacting quantity of the amino groups is relatively large, then a precipitation will occur, and many metal ions is half-bridged by a-R main body, and R already has amino groups which can greatly facilitate the ionization of electrons, and an oxidation will be conducted to form anions at the oxygen gas and produce oxygen cations.

NH$_2$ can be half-bridged with hydroxypropylmethyl cellulose (HPMC) to form R-M-NH$_2$:

a. If the reacting quantity of the amino groups and the reacting quantity of the (metal) ions are not too large, then many metal ions are half-bridged with a-R main body, and connected to an electric hole, for moving the ionized electron to an opposite direction, and thus a degradation will be conducted to form a PVA hybrid, and increase the level of polymerization. It tends to have a gelation, and the adsorbility of the structure is increased, and the high temperature carbonization can be used as an absorber.

b. If the reacting quantity of the amino groups and the reacting quantity of the metal ions are large, then NH$_2$ shows a bridge (ionization and jumping) on the metal-polymer hybrid, and by then the sensitivity of condensation is enhanced significantly, and the reaction can be conducted when it is dried.

c. If the reacting quantity of the amino group and the reacting quantity of the metal ions are small, then R-metal-NH$_2$ cannot be connected to form a reaction mechanism, and both will jump back and forth, and a slow condensation will be conducted.

d. If the reacting quantity of the amino groups is large, then the stability of the solubility of bacteria and enzyme will be high, because the bacteria and enzyme are dissolved by nitrogen.

Further, if the reacting quantity of the amino groups is large, the main body R—OH will be dechlorinated and dehydrated by the metal ions to form R—NH2, or the main body already has amino-NH$_2$ groups; if the reacting quantity of metal ions is large, and the main body R—OH will be dechlorinated and dehydrated by the metal ions to constitute a stable polymer metal hybrid. If the number of metal ions is too small, then the hybrid will be unstable. If the number of metal ions is too large, a hybrid precipitate will be produced. Therefore, the number of metal ions and the number of allocated amino groups will form hybrids to push and pull electrons to flow towards the moving catalyst for the reaction of gas or chemical substance. The reaction mechanism caused by the hybrid structure pushes electrons and pulls electrons by electron receivers or donors instead of by hydrogen receivers or donors. The reaction is not a reaction at a neutral state conducted for several times, but it is a reaction at a catalytic state conducted for an unlimited number of times.

Now, the chemical solution and chemical state and chemical molecular structure are the same as those of chitosan which is a polymer hybrid and will become an artificial imitated chitosan solution containing metal ions and then bacteria or enzyme or smaller nucleic acid or partial cell body is added. It is not necessary to consider its nutrition sources and metabolism issues After being blended and shaled for a period of time (which is determined by the size of the reaction tank, and generally equal to two weeks), the metal ions excite the activity of the enzyme, and a rear end of the NH$_2$ group is connected to a protein enzyme, and an amino polysaccharide such as molassesm with a quick fermentation growth life, a super high concentration, a highly active cell body or bacteria or enzyme or nucleic acid solidifies a carrier to produce a biochemical solution having cell body or bacteria or enzyme or nucleic acid. If the solution of artificial imitated chitosan has a hydroxypropylmethyl cellulose (HPMC) with a higher molecular weight, the stability of bacteria or enzyme stability will be high, and the life expectancy will be long, and it will not be saccharide easily. If the molecular weight is low, then the CPS400 will be as follow:

Just like a common chitosan, it will be saccharide easily to turn into glycan, bacteria or enzyme, and the preservation cannot last too long, and its life expectancy is about one year. In general, the life expectancy of a normal pure chitosan solidified enzyme is very short, but the life expectancy will become one year if the metal ions are added, and the life expectancy will be even longer if humic acid is added to the metal ions to cope with the amino groups. However, the imitated solution of hydroxypropylmethyl cellulose (HPMC) synthesized under CPS400 is simply like the common chitosan that has a higher compatibility with human body, and primarily uses calcium. If the hybrid is stable, the solution can be used as a gauze for the medical treatment of human body. For the solution synthesized at CPS400 or above:

In the CPS75000, the larger the CPS, the higher level is the hybrid polymerization, and the more oleophilic is the CPS75000. It is soluble in water with a disperability and its life is unlimited and forever, so that it can be used in related chitosan of cell body or bacteria or enzyme or nucleic acid used for preserving system, duplicating system, environmental protection, chemical engineering, cosmetics, biochemical, agriculture, fishery, and livestocks, and such artificial imitated chitosan solution containing metal ions can be used. If the diversity of the ecological environment of living things including bacteria or enzyme state is taken into consideration, the expiration for those using CPS400 is preferably set to less than a year. If it is used for the fermentation, a chill spray can dry the solution into a solid state for the application and manufacture of chitosan. Another method uses carboxyl resins to substitute acetic acid to dissolve HPMC, so as to achieve the same result as described above.

Further, the compound or polymer in the metal-polymer chelate can use the plant fiber and/or the carboxyl resin including a carboxyl group for the dissolution, and ammonia is added to the bridge compound or polymer of the metal ions for driving the amino solution, and then the carboxyl resin or plant fiber can be performed with a solid-liquid separation and purification to produce an amino metal compound or an amino metal polymer. Such amino matter is at a polarity state and provides various different applications. If the foregoing metal-polymer chelate uses plant fibers and/or carboxyl resins including carboxyl groups as an acid for the dissolution for the fermentation, ammonia or amino resin or inorganic matter such as polylysine or aminosilane will be used as an amino bridge, and a solid-liquid separation is conducted after the fermentation to obtain amino nano metal polymer or amino nano metal compound or nano metal polymer or nano metal compound or amino biological protein or pure biological protein, and their application will be used as described below.

In view of the description above, the hybrid with a larger molecular weight gives a longer stability for the bacteria, and the hybrid with a smaller molecular weight gives a shorter stability for the bacteria, because the hybrid with a larger molecular weight provides electrons a larger space for the ionization of the hybrid. Throwing a ball (electron) with hands and feet comes with a larger force and a smaller frequency. The hybrid with a smaller molecular weight provides electrons a smaller space for the ionization of the hybrid. Throwing a ball (electron) with hands and feet comes with a smaller force and a higher frequency, and each has its merits. Throwing a ball (electron) with hands and feet comes with a larger force, a smaller frequency and a more powerful polymerization. As illustrated by the embodiments, throwing a ball (electron) with hands and feet comes with a larger force, a smaller frequency, and a more powerful capacity of the oxidizing degradation.

From the description above, the anions of the reacting solution produced at each stage of the condensation, oxidized condensation, and oxidation form a film. In the condensation, the electric conductivity is different, and the electric conductivity is small, and the electric resistance is large. In the oxidizing condensation, the electric conductivity is moderate, and the electric resistance is moderate, and if the film formed in the oxidation has friction (clean gas is passed), the electric conductivity of the anion will be large and the electric resistance of the anion will be small (where the normal leather film is non-conducting), and thus we use different reactions at different stages to fit different gases. If the electric resistances at different areas react with the contaminated gases, the reactions at different stages will have fluctuating electric resistance. If it is condensed to a dry absorption reactant at the air sucking pipe, it has a specific weight and a constant electric resistance, and thus the solvent gas is absorbed when the air pump of the air pipe is started, so as to form suspending colloidal particles fixed on the absorbent, and the mass of the absorbed solvent gas is increased at the air pipe including the absorbent, and the electric resistance of the air pipe will be increased. The larger the concentration of the solvent gas, the larger is the mass of solvent gas to be reacted to form the suspending colloid, and the higher is the electric resistance. The method of increasing the electric resistance to a larger value to compare the increase of mass, and then converting the concentration (for a mid-sized single gas molecule, the complex gas of the same kind uses the total amount of hydrocarbons for the measurement). Similarly, the same applies to the oxidizing condensation (for a mid-size single gas molecule, and the gas has a high stability and free of radicals, the complex gas of the same kind used the total amount of hydrocarbons for the measure, when it is necessary to perform the oxidization before the condensation). If anions are produced in the oxidation and the formed film has friction (clean gas is passed), the electric conductivity of the anion will be large, and the electric resistance will be small. If it is reacted with the contaminated gas, the produced anions will be consumed, and thus the electric conductivity will become small and the electric resistance will become large. From the increased value of the electric resistance, we can know the quantity and concentration of the consumption. The concentration is set to zero if a clean air is passed, we can obtain the concentration by the consumption (For a small-sized single gas molecule, the complex gas of the same kind uses the total number of hydrocarbons for the measurement).

For example, the molecular weights of the hydroxypropylmethyl cellulose (HPMC) system in Embodiment 5 have different viscosities: cps75000 and cps400 and result in a hybrid with a larger molecular weight and a hybrid with a smaller molecular weight as well as a condensation and an oxidizing condensation, wherein the metal salt of copper sulfate is used to increase the electric conductivity. In the same formula, the graph of the relation between the electric resistances of different reactions is plotted, and instruments are used to correct the positive electric resistance and the increase of mass and the concentration of gas, and then a microcomputer is used to compute and display the correct data. Similarly, the anions produced in an oxidation as illustrated in Embodiment 1, if the complex gases of different kinds (referring to the mid-sized solvent gas molecule and the small-sized gas molecules such as $SO_x$ and $NO_x$) are tested, the anions produced in the oxidation as illustrated in Embodiment 2 oxidation are used as a probe, because the air friction at its film produces anions for the small-sized gas molecules as well as the mid-sized gas molecules for the oxidizing condensation. The unique graph of the electric resistances can measure the concentration of the total consumption of hydrocarbons in the complex gases of different kinds, and this kind of probes can measure the polymer gas such as the smell of plastics. The polymer gas requires a strong oxidizing degradation for the mid-sized gas molecules and a set of oxidizing condensation is performed to remove and process the graph of the electric resistance of the polymer gas versus the concentration, so that it can be used for detecting the gas concentration. If this system is used together with nano carbon tubes, the electric resistance and sensitivity of the gas can be identified more clearly.

Further, the fermentation at the metal-polymer chelate(s) is developed to produce a biocatalyst for the metal enzyme. Traditional metal enzymes are fermented enzyme compound plus metal ions, and their life expectancy is limited, but the life and activity of the fermented enzyme of the metal-polymer chelate(s) (such as the hydroxypropylmethyl cellulose (HPMC) system) can be extended unlimitedly, and it becomes a high-performance, high-level, metal biocatalyst. A specially made metal biocatalyst is added to different reacting solutions according to different reactions, and the catalyst provides a synergy for the processing of gas or chemical substance. This solution can add other precipitating agents, or add an alkali, or add excessive metals such that it can be precipitated, or add adsorbent to promote the precipitation, such that it is converted to a solid metal enzyme biocatalyst.

From the description above, a carboxylic acid including a —COON group dissolves chitosan or hydroxypropylmethyl cellulose (HPMC) or the R—$NH_2$ includes an amino group just like the humic acid already having a carboxyl group, so that the whole solution has the amino (alkaline) group as well as the carboxyl (acidic) group, and the so-called positive and negative molecules for driving the catalysis of the whole solution. In the formation of hybrids, the negative molecule and positive molecule are adjacent to each other and gradually developed to tens or hundreds of hybrid tissues, just like the form of protein tissues. The amino acid also has an amino (alkaline) group and a carboxyl (acidic) group, and they are connected linearly to form circular bond to provide a unique configuration for each protein. Since the hybrid solution and protein tissue provide a very good compatibility for the positive and negative charges and are developed to carries of the protein substances such as cell, bacteria, enzyme, nucleic acid, DNA and RNA. If chitosan (already having an amino group) is bonded with the R—$NH_2$-(metal ions) of the hybrid structure, humic acid, and the (dehydrated-OH radical) of the hydroxypropylmethyl cellulose (HPMC) is bonded with R-metal ions-$NH_2$ of the hybrid structure, and the electrons of the two will move in different directions, and thus causing different catalyses and sensitivities. Further, the proteins are dissolved preferably with an electric potential suitable for each protein.

If the solution has not been dissolved by carboxylic acid, a fatty acid is used as the main body and "R" becomes a micro metal hybrid including amino groups, and thus it is not suitable for the growth of bacteria protein. It has the function of suppressing bacteria and can be developed into a quaternary ammonium salt which is suitable to be used as a disinfectant. For example, the butter goes through a saponification to form the butter with sodium salts. With a trace of metal ions, the amino group becomes a hybrid salt with many $NH_2$ functional groups. With the strong dragging force of $NH_2$, a powerful disinfectant is produced, and it can work together with a dilute sulfuric acid as a penetrating agent or a medicinal extract or a solvent for skin treatment, environmental sanitization. This disinfectant including an amino group that attracts bacteria protein easily, but it cannot duplicate the carboxyl group of the bacteria. The disinfectant shows a polarity state for stabilizing the bonding forces of the protein including the hydrogen bond, ionic bond, hydrophobic bond, disulfide bond or Van der Waals force, and the bonding force of the secondary bonds is damaged, such that the protein will be decomposed and denatured, and the bacteria will be killed naturally. Therefore, it is a very good disinfectant.

If the solution of other polymers (chemical substance-OH)n has functional groups or the solution of other polymers (chemical substance-OH)n having functional groups already includes the —$NH_2$ amino group, then the main chemical composition of these solutions has a carbohydrate structure such as chitosan, humic acid, and droxypropylmethyl cellulose (HPMC) that can be fermented, and if the main chemical composition is not a carbohydrate structure, then carbohydrates are added to assist the fermentation. The molecular bond includes asymmetric carbon atoms featuring a special helix structure and a high stability of fermentation stability, and the monosaccharide or disaccharide can be added. The stability becomes very high and the life expectancy becomes very long, after the monosaccharide is added. If PVA already has a trace of acetic acid radicals, some acetic acid is added, and metal salts are added into the water solution, then the solution will be dehydrogenated and dehydrated, and blended at a high speed while the ammonia water is added slowly to form the hybrid. Carbohydrates such as monosaccharide are added and mixed evenly, and then the growth of bacteria or enzyme or tiny nucleic acid or partial cell body can be maintained, and its solidified structure includes: PVA-metal M-$NH_2$-protein enzyme-sugar, which is R-M-$NH_2$-protein enzyme-sugar, and such structure can preserve the bacteria with a long life. Since the PVA does not have asymmetric carbons, it only can maintain the life of bacteria without a good duplicating capability. If there are asymmetric carbons in the aforementioned situation, the life of bacteria can be maintained and a good duplicating capability is provided as well. Further, a polymer unit that is not saturated with fatty acid is taken for example, and an oil is added into the acetic acid, pure water, metal salts, ammonia water, monosaccharide and mixed evenly, and then bacteria or enzyme or smaller nucleic acid or partial cell body are added for the growth of fermentation, and its solidified structure includes: fatty acid-M-$NH_2$-protein enzyme-sugar, and such structure can maintain a long life for the bacteria. In fact, the hybrid of carboxyl and metal ions of the fatty acid and the hybrid structure produced by the allocated amino groups can solidify and fix the enzyme protein, since this fatty acid includes high-carbon molecular R, and others include organic carboxylic acid. If there is no R that includes more carbons, and thus it cannot produce hybrid at a leading position, and thus the structure of this type of fatty acid-M-$NH_2$-protein enzyme-sugar is a reprint of cell tissues.

In a human body, the food source: oils (fatty acids), minerals (metal ions), proteins (amino sources), enzymes in the body, carbohydrates (rice and noodles), acidic matters (organic carboxylic acid such as onion and lemon) are matters that constitute the human body cells, and various stem cells of a human body including nerve stem cells, skin stem cells, embryo stem cells, different stem cells of internal organs. The development of these cells goes with the development of different protein enzymes, and thus the repair of human body cell requires this type of fatty acid-M-NH2-protein enzyme-sugar structure. For dietic treatments, it intentionally lacks the matters of this carboxylic acid, to suppress the quick expansion of enzymes in a human body, and the cells in the body will be composed more slowly. By then, the growth of bacteria in the human body can be suppressed. For example, such dietic treatment for a long period of time can control the disease of AIDS and cure by supplying enzymes to the patient's body. The quantity of enzymes in an AIDS patient's body is much greater than the quantity of enzymes, and thus the AIDS disease will disappear from the patient's body during the process of metabolism n body. For example, the cells in a kidney are recovered by detoxification, and the aforementioned dietic treatment method is used for the control. The patient takes the food containing the foregoing acidic matters and enzymes for supplementing the enzymes in the cell body of the kidney. As a result, the kidney function can be recovered, and this method can be applied for the area of medical science. Taking the growth of a seed for another example, the seed includes fats (fatty acids), proteins (amino sources), starch (carbohydrates), fertilized ovules (nucleic acids) as well as minerals (metal ions) and acidic matters (organic carboxylic acids) from the soil for the germination and growth of the seed. After the seed grows, a tumor in the plant includes an opines matter such as Octopine Family or Nopaline Family, which are mid carbon (alkyl) carboxylic acid, and are structures constituted of R-M-$NH_2$-protein enzyme-sugar to drive the cells to continue their division, and these structure even can create cytokinin and auxin that include monosaccharide bimolecule and important chemical substance for growing the plant continuously.

Further, the industrial oil products include OH radical, and the fatty acid of the industrial oil is accomplished by the foregoing fatty acid-M-$NH_2$-protein enzyme-sugar structure, wherein M stands for different metal ions, and calcium is the safest element for this purpose, and the protein is fermented to form an emulsified oil that can act as an additive to dissolve gases or fuels. The fermentation of proteins can promote the combustion or decomposition of the oil, and calcium ions in the fermentation is turned into a nano scale, such that if an engine is ignited, the fermentation of proteins and the spontaneous combustion changes the calcium ions into nano calciums, and provides a complete combustion for the oil, enhance the horsepower, and lower the pollution. The nano calcium can decompose waste gases and will not hurt human bodies. For example, this kind of emulsified matters such as the fatty acid-M-$NH_2$-protein enzyme-sugar can be added to a lubricating oil to dissolve the lubricating oil as an additive, such that if a cylinder wall requires a coating of nano metals, then the foregoing formula can coat a layer of nano metal on the cylinder wall if the engine is at a high temperature, wherein the fermentation of proteins primarily promotes lubricating or adhering the metal, and the metal ion becomes a nano metal such as aluminum, gold and titanium or a complex metal. Further, waste food oils are used as engine fuels, if the emulsified oil belongs to this type of fatty acid-M-$NH_2$-protein enzyme-sugar matter, wherein the enzyme can change the volatility of the waste food oils, so that hydrocarbons are vaporized under the engine compression ratio, and then dissolved with the waste food oils and used as a fuel oil or specific industrial and commercial purpose oil products or specific functioned food oil products can use similar methods. Therefore, the foregoing solution is used extensively in oil products.

For example, a disaccharide such as sucrose having a low molecular weight is added with acetic acid, pure water, metal salts, ammonia water and mixed evenly, and then bacteria or enzyme or smaller nucleic acid or partial cell body is added for the fermentation and growth, and the solidified structure includes: sucrose-M-$NH_2$-protein enzyme, and this kind of structure does not need the assistance of carbohydrates, because it already has sucrose, and thus the life of bacteria can be maintained very long. Another protection of the sucrose resides on that the whole dry sugar cane can be cut into small pieces so that they cannot be separated from the bagasse, and the juice of sugar cane will not turn rotten because of the protection provided by such dry sugar cane fiber, and then acetic acid, pure water, metal salts, ammonia water are applied and mixed evenly, and the bacteria or enzyme or smaller nucleic acid or partial cell body can be fermented and grown, and its solidified structure includes: R-sucrose-M-$NH_2$-protein enzyme, wherein R refers to a dry sugar cane fiber (plant fiber). Assumed that monosaccharide, acetic acid, pure water, metal salt, ammonia water are mixed evenly, a polymer hybrid will not show, but only a single scattered micromolecular hybrid shows, and they cannot be connected into a whole piece, so that the stability and constancy of fermentation is very limited. The fermentation used to achieve the metal in a nano scale is not very effective, since the overall current is not driven. If polymer bridging agent or plant fiber or inorganic polymer carrier (including inorganic and organic bridge inorganic polymer or nano inorganic polymer) imitates the theory of a dry sugar cane fiber, the fermentation and metal nano condition of a small hybrid molecule at the connecting portion can be improved. Therefore, the formula also can be applied to the arrangement of mixing monosaccharide, acetic acid, pure water, metal salts, ammonia water evenly and adding polymer bridging agent or plant fiber or inorganic polymer carrier, and it includes R-monosaccharide-M-$NH_2$-protein enzyme, and the linearity of the polymer bridging agents is better and the joining line is linear to form a bond. If the glucose follows the method of the artificial imitated chitosan dry powder having no acetic acid can become an artificial imitated glucosamine showing a R-glucose-M-$NH_2$ structure, wherein R refers to dry sugar cane fiber and/or coconut fiber and/or palm fiber (plant fiber and/or including carboxyl acid fiber and/or including carboxylic resin), M refers to a trace of calcium, and a removal of R changes the structure to a glucose-trace of M-$NH_2$ including trace of calcium glucosamine (amino metal compound), to be used for dietic health care, cosmetics and emulsification functions.

The monosaccharide also has another method, and the monosaccharide and single molecules are combined into a bimolecule compound having monosaccharides, and then acetic acid, pure water, metal salt or ammonia water is used and mixed evenly, and then bacteria or enzyme or smaller nucleic acid or partial cell body can be fermented and grown, and its solidified structure shows the features as follows: it includes monosaccharide bimolecule-M-$NH_2$-protein enzyme, and the life of bacteria can be maintained very long, and thus it can be used for achieving a nano metal, and the nutrition source in a plant is light, water, minerals of the soil, bits of organic hydrocarbons and ionized ammonia nitrogen, and carbon dioxide in the air, and the plant can synthesize sugar including carboxylic acid, and the cytokinins in a plant such as the cytokinin-o-glucosides, and the aforementioned solution together with the specific DNA and RNA of the plant can be used for the photosynthesis of the plant or the electric conduction (substituting the light) can produce a large quantity of specific chemical substance in the plant or non-conducting production (it is necessary to change the DNA carrier and the appropriate reaction mechanism), and different DNAs and RNAs in the plant in different carriers can produce different chemical substances by the photosynthesis. Now, we can control the DNA and RNA of the plant, and the carrier of the plant, and the photosynthesis mechanism and nutrition sources of the plant, so as to produce specific chemical substances of the plant. For example, the production condition of a plant in a fermentation tank controls the light, water, minerals and bits of organic hydrocarbons and ionized ammonia nitrogen, carbon dioxide, DNA and RNA that uses the following cultivation and purification of the biological protein enzyme as a carrier (such as the R-unhusked rice-$NH_2$-protein enzyme system) to combine and include the monosaccharide bimolecule-M-$NH_2$-protein enzyme system, and it also can cultivate the chemical substances required in a plant.

Further, the fiber containing carboxyl acids or modified fibers containing carboxyl acids or carboxyl resins such as amberlite IRC-50, pure water, cereal of a plant such as unhusked rice, ammonia water are mixed evenly for the fermentation of a polymer hybrid, and the smashed unhusked rice includes a glycan matter and calcium and shows a R-glycan matter-calcium-$NH_2$-protein enzyme, which is a R-unhusked rice-$NH_2$-protein enzyme, and R refers to the smashed fiber including carboxylic acid (plant fiber or carboxyl resin such as amberlite IRC-50), and it is not necessary to add acetic acid for very good stability and constancy of the fermentation. This semi-solid matter is filtered to produce a liquid, which is a protein enzyme having no carrier and will not be contaminated easily, and thus it does not require any purification to obtain a solution of high-purity high-yield cell or bacteria or enzyme or vaccine. The solution can be used to cultivate and purify various different biological protein enzymes. Further, the R-seaweed cell wall (containing calcium)-$NH_2$-protein enzyme can follow the foregoing method to purify the solution of high-purity high-yield cell or bacteria or enzyme or vaccine, but it is necessary to prepare the disinfection measures first. Further, the combination of R-peat-calcium-$NH_2$-protein enzyme, solid peat and calcium will not be precipitated, and the peat contains a humic acid with the properties of a glycan matter. The humic acid further contains the properties of carboxylic acid, and thus the peat-calcium-$NH_2$-protein enzyme structure may have R (fibers of carboxyl acid or carboxyl resin) to achieve a high-purity high-yield cell or bacteria solution or enzyme or vaccine, but it is necessary to prepare the disinfection measure for the peat first. For R-hydroxypropylmethyl cellulose (HPMC) and humic acid and calcium-$NH_2$-protein enzyme, the hydroxypropylmethyl cellulose (HPMC) and humic acid and calcium are mixed and gone through a pH-balanced precipitation to form a hybrid solid combined with calcium and filtered and mixed with the ammonia for fermentation to form hydroxypropylmethyl cellulose (HPMC) and humic acid and calcium-$NH_2$-protein enzyme. Such structure may have R (fibers of carboxyl acid or carboxyl resin) to achieve a high-purity high-yield cell or bacteria solution or enzyme or vaccine. Further, the R-chitosan and calcium-$NH_2$-protein enzyme can follow the foregoing method to purify the solution if high-purity high-yield cell or bacteria or enzyme or vaccine. The required enzyme solution can be filtered from the carrier, and those not used will be put back to the carrier for bridging and preserving the activity of the enzyme solution. Particularly, some vaccine or enzyme cultivation used for human bodies and animals does not require a carrier system accompanied to enter into a human body, and this kind of purification is the most appropriate one because it is much simpler and easier than the technologies of affinity chromatography and anion-exchange chromatography (HPLC). If the fermented and purified matter does not need any remaining amino groups, the suspension and cultivation of amino resin or inorganic matter such as polylysine or aminosilane can substitute ammonia for the fermentation, and then the purification (pure biological protein) is a typical application of the solution of metal-polymer chelate(s) for the cultivation and purification of biological cell or bacteria or protein enzyme.

Similarly, the foregoing technology of carriers having biological cell or bacteria or protein can be used for the cultivation and purification of non-protein such as bacteria metabolite and products, and the cultivation of general bacteria metabolite and product is to add a nutrient agent into the bacteria solution, so that the life cycle of the bacteria includes metabolism and growth, and the life cycle, growth, progress, and cultivation method and medium are designed according to the required metabolite. The quantity of carrier systems in accordance with the foregoing technology is the major factor for controlling the metabolism and growth of the bacteria. Different metabolism requirements fit different carrier systems, and the number of carriers can control the growth rate of bacteria and the required nutrition for the metabolism and the metabolic product. For instance, the more the carrier, the faster is the bacteria racing for the nutrients, and the slower is the metabolic rate. By then, it is appropriate for the antibiotics in the bacteria to be cultivated. The less the carrier, the more is the productions, and the more is the nutrient. The metabolic growth will become stable, and the yield will be stable. The half cycle achieved by the carrier system in accordance with the foregoing technology is very long, and is almost unlimited. It is one kind of biological reactors capable of continuously performing the biotransformation by a mobile blending reactor or a fixed-bed reactor or a moving bed reactor or super filtering film separating reactor, and the metabolite can be filtered and separated easily, and the purified metabolite can be removed by the bacteria in the body by microfiltration or disinfection or other method. Another kind of biological reactors is a fatty acid-M-$NH_2$-protein enzyme-sugar in a semi-solid gel (a filtered solution including carboxylic acid) mixed with a R (a fiber having carboxylic acid or carboxyl resin) can imitate the tissue of human body or animal cell, which is condensed and bridged like internal organs and fixed in the included layers. By then, the slow loop refers to the nutrition solution, and a specific metabolite is cultivated, and then the cultivation is specified. The description above shows a solution of metal-polymer chelate(s) used for the cultivation and purification of the biological cell or bacteria or protein enzyme and their metabolites.

Further, the disaccharide, acetic acid, pure water, metal salts, and ammonia water are mixed evenly to give the stability constancy of the fermentation of a polymer hybrid. The invention can be used to obtain a metal in a nano scale. The maltose having no asymmetric carbons is arranged symmetrically in zigzag shaped units due to the short —OH bonds, and these zigzag shaped units are arranged alternately into an object similar to a filtration cloth for providing a more powerful tension for the solution, and the pores on its warps and wefts allow nano components to pass through and the liquid soaked into the film of the cloth is dried to produce a nano filtration cloth. These zigzag shaped units are suitable for objects with a smaller atomic radius. Since the space defined by the hybrid is very small, therefore an object with a larger atomic radius cannot pass through, and even bacteria cannot pass through. Other polymer metal hybrids can be filtered but the filtration will be irregular and will not have lines similar to a woven cloth.

In this series of applications for the fermentation for genetic engineering, the DNA and RNA can be duplicated quickly. Unlike the prior art that requires complicated procedures for cultivating DNA and RNA, the foregoing eight major enzyme systems have different interfaces, so that when two different cultivating interfaces are adjacent to each other, variations will occur during the process of duplicating DNA and RNA. From these variation, we can learn the adaptability of DNA and RNA at different cultivation tissues, and the DNA and RNA in human body fit the cell tissue of human body, and those of animals fit animals, and those for plants fit plants, and those for species fit species correspondingly. Therefore, the invention can be used for duplicating DNA and RNA, studying variations, and developing special gene-cell tissues. For example, if a cell of the epidermis of a human body is bitten by a bug, then new protein enzyme is injected to show a swelling. The SARS proteins and fruit foxes can coexist, but the varied proteins will behave irregularly in the carrier of the cells in human body cell and the adaptability does not exist anymore. In other words, we are sure that the variation of the gene-cell performance shows us that the fruit fox and the carrier of the cells of human body are different. For example, the bird flu will be varied to infect a human body, and a long-term cell carrier is incompatible to a 45-day growth hormone, and thus the size and stability of the enzyme and the adaptability of the carrier of cells are related to the performance of the genes.

Therefore, special applications for gene-cell tissues can be developed. Chitosan exists in nature, and exists in human body just like a cell repairing the tissue of a human body, such as glucose or glycan-protein exist in the tissue of a human body. The imitating chitosan solution of metal ions can also imitate the tissue of a human body to develop the cultivation of cells and reproduction of nucleic acid and DNA, e.g. the humic acid, when the metal ions (inorganic salts) is used together with an amino group, the plant added to the amino group will grow faster and stronger than that without adding the amino. For example, when an injured dog with an exposed bone on its thigh has applied chitosan and a trace of metal elements, its effect will be much better that using the separate chitosan alone. Soon after, the dog's skin and muscle will grow; for example, in the cultivation system of the hydroxypropylmethyl cellulose (HPMC), there will be no problem to cultivate single-cell blue-green algae or yeasts by using the fermented grown bacteria and enzyme solution, breaking the insect egg and putting it into the solution. More nano DNAs and RNAs are reproduced and cultivated at the top surface to form the helix shape, which is different from the original bacteria and enzyme. Evidently, such kind of solution can be developed in a variety of proteins. As for the cell tissues, they are featured with a variety of proteins and used to develop diversified tissue cultivation technologies.

The abovementioned series of fermentation solution is compared with the culture medium of the tissues of an invertebrate, much faster and capable of establishing a pure family of cell clusters. In such a solution, partial metal ions can be mixed with different inorganic salts (added respectively), depending on the cultivation requirements. After reproducing the cell, plants are transplanted in the culture medium for roots growing, while animals are transferred to the culture medium for growing. The cultivated cell solution can be mixed with the nutritious solution, and then the cell tissue will continue its development on it. For chicken feeding as an example, using the feed developed by the structure of the fatty acid-M-$NH_2$-protein enzyme-sugar with an addition of enzyme accelerate, chicken can be grown up rapidly within 45 days without any side effect. Therefore, we can use it to develop the rapid culture of animals and plants and the sexless reproduction technology.

In the nano technology, usually it remains 10-6 nano after a metal solution is dried. To achieve a nano scale of $10^{-9}$ m, a sol-gel method for transforming the solution to an organic metal first. The chemical process is difficult and confiscated as well. However, nowadays the protein enzyme is almost of the nano scale, and in the aforesaid enzyme system or hydroxypropylmethyl cellulose (HPMC) enzyme system, the internal R-metal ions-$NH_2$-protein enzyme is at an interactive state. Since the protein enzyme will be fermented into the metal hybrid system to form an organic metal and in the solution the positive attraction force and an opposite attraction force will be mutually attracted, and it will lead to a miniaturization of metal ions and a nano scale. Using this technology, different kinds of metal ions can be nanonized for a variety of applications in different fields. In principle, a protein enzyme with a nano scale can have more nano metals and vice versa. If the nano quantity is smaller, its nucleic acid will be even smaller. The quantity of nano metal can be set. Some different protein enzymes have different metal crystal-phases. Those protein enzymes eating up heavy metals can even create a special crystal-phase structure. Hybrid with a higher molecular weight and that with a lower molecular weight will get different crystal-phase structure based on the same bacteria fermentation. For obtaining high yield of nano metal, metal ions with highest rate approximately equal to 10% can be added into the enzyme system or add 10% fermentation first then add some metal ions, however, the fermentation should be carried out during mixing procedure to avoid any precipitation. For obtaining smaller nano quantity, the metal ions specified in the hybrids table should be dosed. In the reacting solution forming hybrid, if the metal ions are impossible to be combined, it can be heated and mixed evenly; or for metal ions with smaller ion radius, they should be added and mixed with other metal ions; or after half fermentation of a trace of iron ion, add the metal ions which are difficult to be combined, for the purpose of continuation of fermentation and forming. Later, to obtain the nano iron. For obtaining metal, using the magnet to separate the iron for purification; or adjust the pH value to get the hybrid combined, structure tends to be stable etc. The nano metal protein is coated or sprayed onto the enzyme cloth for a dry thermal decomposition or a flame spray is performed for killing protein enzymes at a high temperature, or being partially combusted into a nano film or sintered without oxygen carbonization to remove the organic matter to form a metal carbonate or oxide;

or in the water solution to add thermal decomposition, then add precipitating agent;

or in vacuum state the liquid get vaporized to decompose the compound metal gas, then recycle by condensation;

or to be added in an oil pot for thermal decomposition first, then add water for cooling, precipitation and recycling;

or in the liquid using the oxidizer, O-2strong oxygen degradation hydrocarbon and amino to get the $CO_2$, $H_2O$, $N_2$ gases flown away.

Finally, only the nano metal particle or nano metal oxide or nano complex metal oxide will remain (for obtaining the complex metal, when adding the fermentation solution, the complex metal should be independently mixed evenly first prior to addition) for further application or the following purposes. Because the nano metal particles can remove the chemical substances, such as the dechlorination function; Nano oxide powder is featured with higher surface area and higher distribution of porous volumes and therefore, has excellent adhesion ability to solvent. The titanium catalyst solution is a practical case study. When the titanium sulfate and the acid dissolved hydroxypropylmethyl cellulose (HPMC) together with the amino have made a catalyst solution, after fermentation the titanium ion can be nanonized, after coating the Ti compound in the hybrid after half combustion tends to Ti oxide, and become titanium dioxide powder film.

Solution of metal-polymer chelate(s) to be added with silicic acid first to become the PVA-silicic acid-metal M-$NH_2$-protein enzyme-sugar, it is the R-silicic acid-M-$NH_2$-protein enzyme-sugar. The —OH radical of the Rand silicic acid and the metal M together with hybrid, after fermentation, the metal will get nanonized. The silicone (Si) can also be nanonized, and can be extended to become a nitrified silicone, carbonization silicone, siliconized complex metal nanonization, using nano material production heat treatment or during the ceramic firing reaction process to add nitrogen or shortage of oxygen or add other nano solution of metal-polymer chelate(s) to yield the nano silicone compound or to be mixed directly into the ceramic processing technology to produce the nano complex ceramic material. Additionally, for example, the solution of metal-polymer chelate(s) after fermentation, the metal can be nanonized; or in the ceramic process the fermentation solution of metal-polymer chelate(s) to be added directly, and in the firing process to get the desired nano complex ceramic material, one can see the setting what kind of nano powder is mixed evenly in there or the intention to obtain the pure nano powder to form nano ceramic. Then it is heated or ore-sintering and is mixed evenly or in the reaction adds in oxygen gas then the nano- oxidized metal can be obtained. Or add in nitrogen gas just like mixing in nano nitrified metal. By adding fluoric acid, then the nano fluoride metal can be obtained. By obtaining phosphoric acid, then the nano phosphoric acidic metal can be obtained. Based on these, one can separate and precipitate or generate crystal or mix this into the ceramic craft to produce a nano complex ceramic material and nano complex ceramic can be made to use the fermentation solution of metal-polymer chelate(s) (that can be mixed in many type). In the course of dispersal, it has already possessed moisturized powder and after mechanical dispersion and stabilizing, mixing can be conducted by means of colloid grinding machine. Amongst these the fermentation chitosan or hydroxypropylmethyl cellulose (HPMC) or polyvinyl alcohol nano system can all possess the characteristic of cohesive agent so that the dispersed mixed can be more stabilized and can avoid reunion phenomenon. It can control the turbid solution quality so that the base structure can be even to enter into form (press forming, casting forming) and ore-sintering or simultaneous proceeding of forming and ore-sintering. During ore-sintering, the wrapped and moist solution of metal-polymer chelate will form carbonization like carbon black wrapping combustion and in the heat treatment, the carbon black will be oxidized. The ore-sintering in the course of ore-sintering the most important is control pressure and temperature. The ore-sintering is separated into reaction ore-sintering, atmosphere ore-sintering, heat pressure ore-sintering, discharged plasma ore-sintering, ultra high pressure ore-sintering and heat static pressure ore-sintering and high pressure ore-sintering and high pressure gas phase reaction ore-sintering etc. What kind nano structure and product is required use with the above ore-sintering method. In the most important course do not have reunion and crystal growth coarse to obtain high quality nano ceramic. For example, for the titanium oxide solution of metal-polymer chelate(s) (fermentation hydroxypropylmethyl cellulose (HPMC) system) at 50° C., correspondingly the humidity is 60%, the titanium oxide gel is obtained. After pouring forming on the gel of the biscuit of titanium oxide can be obtained. The biscuit obtained will have ore-sintering when it is closed to the anatase phase rutile phase change temperature that means under 600° C. and obtained corresponding density of 99%. The size of crystal grain is only 60 nm nano ceramic and under general condition, the density temperature of nano is between 800-1000° C. By dense ore-sintering under 600° C., it will sufficiently utilize the function of solution of metal-polymer chelate(s) during phase change of nano. Although the temperature of 600° C. is comparatively, yet as the energy generated from phase change will promote the proceeding of ore-sintering and still can obtain dense nano ceramic.

The nano solution of metal-polymer chelate(s) or multiple type of nano solution of metal-polymer chelate(s) (already under fermentation) will spread evenly to plastic or rubber polymer, polyamide, polyethylene, polystyrene, epoxy resin, silicone—etc. as the basic material or series of mixed base material and the dispersal method is as follows:

Nano solution of metal-polymer chelate(s) itself is assembled liquid and solution plastic or powder form plastic or melted plastic or polymer vanguard small molecular solution evenly mixed including mechanical dispersion, ultrasonic dispersion , high energy processing method and chemical dispersion.

Mechanical dispersion: plastic membrane dispersion, high speed mixing and based on the aiding chemical function to heat and vaporize so as to enable separation of metal hybrid and to combine with plastic polymer.

Ultrasonic dispersion: supersonic waves will damage the enzyme and hybrid structure of the nano solution of metal-polymer chelate(s) so that the nano metal is particle that will combine with plastic polymer sufficiently.

High energy processing method: by mixing in colloid or monomer dispersion and through the radiation chemistry function including corona, microwave, plasma, ultraviolet ray etc. (some can promote fermentation) and through heating and vaporization, the metal hybrid will be combined with plastic polymer to combine or simultaneously contract the assembly.

Chemical dispersion: add surface chemistry modifier or compatibilizer or breaker such as hydrochlorous acid solution and afterward mix this into the nano solution of metal-polymer chelate(s) and plastic polymer so that the metal hybrid can separate and combine with plastic polymer.

Another method is to base on monomer mixing of nano solution of metal-polymer chelate(s) and plastic polymer, then use the additional polymerization or contracted polymerization or combination solidification and will heat and vaporize to have a mixed forming.

Another method is based on various single mixture and plastic polymer (or carboxyl resin such as Amberlite IRC-50) before the end fermentation or its monomer mixing combination. Then use fermentation and the above feasible dispersal (fermentation will not be interfered with) or in the fermentation add polymerization or contracted polymerization or cross united solidification (referring to fermentation with no interference and will heat and evaporate so that it can become a mixed forming.

In another method of nano solution of metal-polymer chelate(s) and polymer latex solution mixing such as dispersal of latex grain of latex . Then add in the flocculatin agent to disperse so that the entire system can be sedimented, centrifugal separation or water dehydration, heat dry and vaporize.

However, all these will consider the stability design of the nano complex material and base on the chemical structure of polymer and the surface electric charge of nano particle of broken belt and incomplete key, there will be formation of common value chain between the two and will be achieved based on ionic bond, position key or parents and function.

For selective system there is chitosan or hydroxypropylmethyl cellulose (HPMC) or bicarbohydrates or monocarbohydrates, or degraded oils or polyvinyl alcohol or humic acid or mixed or other etc. nano metal-polymer chelate system solution to promote reaction. Especially in some plastic add some fatty acid-M-$NH_2$-protein enzyme-sugar and this system can cope with other system so as to promote blending.

When metal-polymer chelate has carboxyl, and on top of R—$NH_2$ including amino, such entire solution will possess amino (alkaline) as well as carboxyl (acid base) and clay mixed to obtain organic clay similar to amino acid. At this time, fermentation is feasible and then combines with plastic and rubber polymer with multiple compatibility.

The above dispersal method can separate or can combine with mixed use. The overheating evaporation or other heat melting press forming requires heat vaporization so that the metal hybrid will collapse and combine with plastic polymer. The forming methods can be separated into pressing forming, solidification forming, extraction forming, injection molding forming and injection forming etc. The above dispersal method can also be used in nano material production. The above requires adding of oxygen gas in heat reaction to obtain nano oxidized metal or to obtain nano carbonization silicone by oxygen deficiency or add in nitrogen gas in the reaction just like mixing in nano nitrified metal. The addition of fluoric acid can obtain nano fluoric metal. The addition of phosphoric acid can obtain nano phosphoric acid chemical metal. These can be directly mixed in the plastic polymer.

For example, by using the nano solution of metal-polymer chelate(s) in the humic acid-metal zinc-$NH_2$-protein enzyme and for the manufacture of nano complex rubber in the complex rubber is to adopt mechanical filling dispersal method. In the rubber base, the humic acid-zinc-$NH_2$-protein enzyme will exist in the form of separated and assembled body and it will have a cross unity enhancement function. For the humic acid-zinc-$NH_2$-protein enzyme of the nano class assembled enhancement rubber, there are a few characteristics: there is a certain compatibility as rubber and there is suitable reaction activity with rubber. There is a certain self assembly ability. The even assembly matter of the separated assembly body has a better inner assembly ability. The induction of rubber is to enhance the cross unity efficiency (including cross unity speed and cross unity density). To improve the structure of the cross unity key (induce more ion cross unity key), one on hand it will generate joining and cross unity with large rubber molecule and then it will be heated and vaporized in the mixing and blending. The humic acid will complete in the reaction and will form carbonization. Therefore the temperature will progressively enter to high temperature from low temperature. Low temperature is to bring out its reaction and high temperature is because reaction is soon to be completed and the carbonization will disappear. What remains is combination of nano zinc or zinc oxide. For the mechanical function of the nano zinc filling rubber, the stretch intensity of pull is higher. In the nitrile butadiene rubber (NBR) of that form, fill in about nano zinc 10% and the stretch intensity of its vulcanized rubber pull can reach about 55Mpa and this is the highest rubber intensity except the short fiber complex rubber.

Solution of metal-polymer chelate(s) in the application of nano textile industry, nano fiber adding nano solution of metal-polymer chelate(s) (particle) mixed yarn manufacture and coating processing and there is solution of metal-polymer chelate(s) used in textile product in the industry to extend the technology to conduct dye-transfer processing.

Palletization method: in the course of assembly, after adding the solution of metal-polymer chelate(s) produce it as material slice.

Contracted assembly-palletization slice cutting-dry-lever yarn-processing after rolling-polyester fiber.

Injection method: in the yarn processing course, use syringe to add the solution of metal-polymer chelate(s) in the melted polyester fiber and make into polyester fiber. The method is to place the solution of the metal-polymer chelates (dry) into the syringe and then pour in during the lever spinning. Polyester slice cutting-dry-lever spinning-processing after rolling-polyester fiber.

Solution polyester fiber: base material used by solution spinning is mostly polypropylene. Normally the solution of metal-polymer chelate(s) is directly added to the polyester fiber solution to mix with the melted spinning. Also the ceramic inorganic salt can be dispersed to the solution of metal-polymer chelate(s) of the chitosan or hydroxypropylmethyl cellulose (HPMC) system and then conduct further fermentation and then add into the spinning solution.

Implant processing method: the surface micro pore size and shape of the natural fiber and based on different fiber, the pore diameter of these micro pore is mostly and comparatively larger than the inorganic nano grain diameter. On the warp surface, the processed fiber will combine with inorganic nano. The activity of the solution of metal-polymer chelate(s) and natural fiber will generate physical adsorptability and chemical combination.

Coating method solution of metal-polymer chelate(s) will be evenly coated on the top of the natural fiber to form a layer of thick coating membrane. Then after drying and necessary heat treatment, various mechanical natural fiber processing can be conducted.

The aforementioned solution of metal-polymer chelate(s) is characterized in that the solution of metal-polymer chelate(s) used in the nano plastic or nano textile industry includes plastic or rubber polymers, wherein the plastic or rubber polymer is polyamide, polyimide, polyethylene, polyvinyl chloride, polyaniline, polystyrene, polyphenylenevinylene, acrylonitrile-styrene-butadiene, polyethylene oxide, epoxy resin, bakelite, polycarbonate, polypropylene, polyacrylic ester, polyester, polyurethane, polyolefin, polyvinyl butyral, polysiloxanes, pinene oxide (PNO), rubber, nitrile butadiene rubber (NBR), silicone, polyvinylpyrrolidone or its precursor or its oligomer or the foregoing modification and blend system.

Dye-transfer Process: The solution of metal-polymer chelate(s) of a monosaccharide system is a R-monosaccharide-M-$NH_2$-protein enzyme, wherein R refers to a plant fiber or an inorganic polymer carrier (including inorganic and organic bridge polymer or nano inorganic polymer) formed to a nano scale after the fermentation is completed. If R (referring to a plant fiber or a carrier including carboxyl acid fiber or inorganic polymer) disappears, it is a monosaccharide-M-$NH_2$-protein enzyme, and then the life of protein enzyme is not very long and the protein enzyme is less stable. After a brief baking and disinfection, the monosaccharide-M-$NH_2$ is removed. By then, a metal M is in a nano scale and it includes an amino R, and the nano metal matter, is in a polarity state and similar to an azo dye developer R—$NH_2$ that matches up with an azo dye base for an azo coupling, so as to secure the nano metal matter on the fibers without causing any harm to human body. For example, the solution of metal-polymer chelate(s) for a monosaccharide system is placed in a (bridgeable) carrier filled with plant fibers. After a fermentation is completed, the metal is turned into a nano scale, and the solution of metal-polymer chelate(s) is squeezed from the plant fibers under pressure, and the squeezed solution of metal-polymer chelate(s) is baked at 80. c and disinfected by ultraviolet beams, and a dye-transfer process is carried out to the nano metal to coat a base in the dye-transfer process and dissolve the base in the water, such that the fibers are soaked into the base, and then the developer R—$NH_2$ is mixed with the nano monosaccharide-M-$NH_2$ for the nitrification to achieve the functional effect of a nano metal and show the color. These are the applications of the solution of metal-polymer chelate(s) in the nano textile industry.

The foregoing reacting solution is a novel polymer liquid crystal material, and such biological liquid crystal features the mobility of the liquid and the sequence similar to a crystal structure. People discovered that many biological macromolecules such as RNAs, DNAs, proteins, fats, fat protein and polysaccharides have the properties of a liquid crystal, since they are made of a single helix structure and a double helix strict. This fermentation series such as hydroxypropylmethyl cellulose (HPMC) is a double helix structure formed by the fermentation (the hybrid structure not fermented is a single helix structure or this water soluble single helix structure can be used as a liquid crystal. After a nucleic acid is added and fermented, the added protein enzyme becomes a double helix structure) which is more stable than the single helix structure in the solvent. The double helix structure can exist stably without the solvent, and thus it can be developed more extensively. This solution copes with the fermentation by silver sulfate to make a nano silver and obtain a high light transmission rate in the visible light area and a nano liquid crystal solution with a smaller resistance, or becomes a film after being dried. This nano liquid crystal and liquid crystal film electrode can be used in flat panel displays.

The foregoing reacting solution is a novel semiconductor material that can fix a natural electronic component made of proteins or celluloses such as DNA of a plant at a monosaccharide enzyme system including a monosaccharide bimolecule-M-$NH_2$-protein enzyme, a monosaccharide-M-$NH_2$-protein enzyme-polymer bridging agent and uses the characteristic of a plant conducting photosynthesis to develop an organic electroluminescence (OL), and these two major enzyme systems are not fixed so securely, and the activity of enzymes can be strengthened by external forces, and thus it requires plants to receive lights and produce electrons inside for the growth. If no direct light is given for the reaction of the electrons, the reaction will be controlled by the surrounding growing conditions, so as to produce a reverse reaction to emit a light source, or the gene and enzyme of a luminous body of a firefly or an animal in water are used for the development. These are organic EL semiconductor components. Further, the protein chips use the protein molecules of the biological material such as the protein enzyme system of polyvinyl alcohol and goes through a special art to prepare a layered structure of super film tissues. For example, the proteins are used to prepare a liquid of an appropriate concentration, so that the water surface is spread into a single molecular layer film which is then placed on a quartz layer. Similarly, a layer of organic film is prepared to obtain a biofilm with a thickness of several hundreds of nanometers. This kind of film is composed of two types of organic matter films. If ultraviolet rays are projected onto the protein enzyme system of a polyvinyl alcohol of one type of films, the resistance will rise approximately by 42%; and if visible lights are projected, then the resistance will resume its original status. However, the protein enzyme system of a humic acid of another type of films will not be affected by the visible lights, and if ultraviolet rays are projected, the resistance will be decreased approximately by 7%. The different protein enzyme systems of the two different solutions of metal-polymer chelate(s) are combined to produce a biological material which becomes a novel light controllable switch component. This type of film can be used for developing bioelectronic components and creates the applications for semiconductors.

The foregoing reacting solution is a novel biofuel battery material that can use specific gene and/or enzyme to receive lights or other stimulations, and the electron reaction produced inside constantly conducts electrons to accumulate electrons and cause an electromotive force, so as to produce a current, or the enzyme of an electric generating system in the body of an electric eel is used to develop the generation of electricity. For example, the seeds of alfalfa sprout in a plant are originally at a sleeping state, and the alfalfa sprout will be germinated if radiations such as ultraviolet rays are provided. Similarly, the genes and enzymes of the germinating alfalfa sprout are extracted and used for the oxidation of the chitosan-$NH_2$-M-protein enzyme to produce anions, such that it can be dried and coated onto the electrode panel after its fermentation. Once if the electrode is coated with sufficient paints capable of emitting ultraviolet rays, another side of the electrode panel adopts a PVA-metal M-$NH_2$-protein enzyme-sugar system (as a conductive medium film), wherein the metal uses Ru(2) as a sensitizer, and then the electrolyte includes 0.04 mol/L of $I_2$ and 0.5 mol/L of LiI and the other end of the electrolyte is a Pt electrode. If the paint emits ultraviolet hv to excite the gene and/or enzyme of the alfalfa sprout on a chitosan system having an oxidation occurred on the anion system, the energy level of the gene and/or enzyme of the alfalfa sprout will be raised, and the germinating state gives rise to a synthesis having the effect of an electric hole, such that the energy released by the oxidation of the chitosan system discharges anions (electron e), and the energy level h gives rise to an oxidation and a reduction at the electrolyte of the sensitizer of the PVA system and the Pt electrode. Further, the electrons on a nano crystal of the semicondctor electrode film having the oxidation are collected to the electrode surface and transmitted to the opposite electrode through external circuits. In a preferred embodiment of the present invention, 1~4% of the powder hydroxypropylmethyl cellulose (HPMC) with a viscosity CPS equal to 75000 is put into a mixed solution including 1~4% of acetic acid or other acids (including organic carboxylic acid and/or inorganic acid having —COOH groups) and 97~88% of water. At 20° C., a thick liquid of transparent hydroxypropylmethyl cellulose (HPMC) is formed. The thick liquid and 1~4% of acidified or chlorinated or hydroxidized (referring to nitrified sodium humate) or inorganic polymer monovalent, bivalent, or trivalent metal ions (two or more bivalent metal ions can be mixed partially or separately, and the foregoing 1~3% of metal ions and 0.1~80% of acidified or chlorinated or nitrified or inorganic polymer iron ion has the oxidizing capability for the gas) sufficiently blended, mixed, blended at a rotary speed of 200 rpm, become condensation solution and oxidizing condensation solution and other reacting solution.

The formulas for various reacting solutions in accordance with different embodiments of the invention are listed below:

Embodiment 1

In the application of drying an oxidation solution and producing anions by the air friction of the film, the composition is given below:

| | |
|---|---|
| Vinegar | 1.30% |
| Chitosan powder | 1.30% |
| Water | 90.6% |
| Copper sulfate | 3.40% |
| Iron sulfate | 3.40% |

In the formula above, the chitosan must fall within the range of viscosity from CPS 100 to CPS 240, and the polymer hybrids so produced are lower molecular hybrids, such that the air friction can produce anions, and $O^{-2}$ oxygen cations can be detected by a detector. In this formula, the copper ions and iron ions are combined together, and the iron ions in the hybrid are oxidized, and the copper ions at the complex state reduce the oxidized iron ions to provide a half-bridge —R body with many metal ions, and thus the electron streams in the hybrid always greater than the electric holes and electron stems to produced anions continuously.

Embodiment 2(An Alkaline System Already having Carboxyl Groups)

In the application of producing anions by the air friction of a film after the oxidation solution is dried film air friction, the composition is given below:

| | |
|---|---|
| Nitrified sodim humate | 100 mg |
| Copper hydroxide | 2 g |
| Iron hydroxide | 2 g |
| Ethylenediamine | 0.3% |

The detector indicates that there are anions produced by air friction and $O^{-2}$ oxygen cations are included.

Embodiment 3

In a degradation solution, the composition in percentage by mass is given as follows:

| | |
|---|---|
| Water | 94% |
| Vinegar | 2% |
| Hydroxypropylmethyl cellulose (HPMC) | 2% |
| Magnesium sulfate | 3% |

The prepared reacting solution is titrated by 0.05 cc of acetone at the surface of the reacting solution, and the expanded surface of the acetone will be degradated into a tiny plastic film in about 20 seconds, and the acetone will disappear. Repeated processes of the same procedure will get the same result. The reaction time takes longer since the produced electric holes and acetone at a chemical state fall apart slowly.

Embodiment 4

In the application of processing organic solver in a condensation solution (which could be for fermentation and nano applications), the composition in percentage by mass is given as follows:

| | |
|---|---|
| Vinegar | 2% |
| Chitosan powder | 2% |
| Bacteria-free water | 94% |
| Zinc chloride | 2% |
| PVP K-30 | 0.3% |

The prepared reacting solution is titrated by 0.05 cc of acetone at the surface of the reacting solution, and the expanded surface of the acetone will be condensed into a tiny plastic film in about 10 seconds, and the acetone will disappear. Repeated processes of the same procedure will get the same result.

Embodiment 5

In the application of using a dry (free of water) organic to process the solvent condensation solution, the composition in percentage by mass is given as follows:

| | |
|---|---|
| Bacteria-free water | 93% |
| Citric acid or carboxylic acid | 2% |
| Hydroxypropylmethyl cellulose (HPMC) (cps 75000 viscosity) | 2% |
| Magneiusm sulfate or copper sulfate | 2% |
| Ammonia water | 1% |

The prepared reacting solution is titrated by 0.05 cc of acetone at the dry surface of the reacting solution, and the expanded surface of the acetone will be condensed into a tiny plastic film in about 10 seconds, and the acetone will disappear. Repeated processes of the same procedure will get the same result. If the same foregoing formula is applied to the hydroxypropylmethyl cellulose (HPMC) with a cps 400 viscosity, it is found that the hybrid structure with a smaller molecular weight tends to have the oxidation/condensation characteristics, instead of simply having the pure condensation characteristics.

Embodiment 6

In the oxidized condensation solution (could be used for fermentations and nano applications), the composition in percentage by mass is given as follows:

| | |
|---|---|
| Humic acid | 100 ml |
| Copper sulfide | 0.35 g |
| Iron sulfate | 0.05 g |
| Ammonia water | 0.3% |

The prepared reacting solution is titrated by 0.05 cc of toluene at the surface of the reacting solution, and the expanded surface of the toluene will be oxidized and condensed into a tiny dispersing film in about 10 seconds, and then the dispersing film as well as the toluene will disappear. Repeated processes of the same procedure will get the same result.

Embodiment 7

In the application of processing organic solvents in a condensation solution, the composition in percentage by mass is given as follows:

| | |
|---|---|
| Polyvinyl alcohol | 44 g |
| Water | 721 ml |
| Add water after the heating, blending and dissolving processes. | |
| Copper sulfate | 44 g |
| Ammonia water | 26.2 ml |

The prepared reacting solution is titrated by 0.05 cc acetone at the surface of the reacting solution, and the expanded surface of the acetone will be condensed into a tiny plastic film in about 10 seconds, and the acetone will disappear. Repeated processes of the same procedure will get the same result.

Embodiment 8

The biochemical solution used for the fermentation is a metal enzyme biocatalyst as well as an artificial imitated chitosan solution, and their composition in percentage by mass is given as follows:

| | |
|---|---|
| Bacteria-free water | 94% |
| Vinegar or carboxyl acid | 2% |
| Hydroxypropylmethyl cellulose (HPMC) | 2% |
| Magnesium sulfate or calcium sulfate | 2% |
| Ammonia water | 2% |
| Fermenter | Trace |

After being fermented and preserved for many years, it is still effective.

Embodiment 9

In disinfectant solution, the composition in percentage by mass is given as follows:

| | |
|---|---|
| Bacteria-free water | 94% |
| Sodium fatty acid | 3% |
| Magnesium sulfate | 0.01% |
| Ammonia water or urea | 3% |

For example, if the foregoing disinfection solution is applied to the affected part of a beriberi patient, it will take half a day to kill the germs completely.

Embodiment 10

In the application of a bacteria preservation system (also used for preservations and nano applications), the composition in the percentage by mass:

| Bacteria-free water | 82% |
|---|---|
| Vinegar or carboxyl acid | 2% |
| Polyvinyl alcohol | 4% |
| Magnesium sulfate or calcium sulfate | 4% |
| Ammonia water | 3% |
| Carbohydrates (monosaccharide or disaccharide) | 5% |
| Bacteria | Trace |

It is still effective after being preserved for over a year.

Embodiment 11

In the application for food related medical treatments and health care (also can be used for fermentations and nano applications), the composition in the percentage by mass is give as follows:

| Bacteria-free water | 90% |
|---|---|
| Vinegar or carboxyl acid | 2% |
| Fatty acid (degraded oil) | 1% |
| Calcium sulfate and various inorganic salts (added separately) | 2% |
| Ammonia water or protein | 2% |
| Carbohydrates (monosaccharide or disaccharid) | 4% |
| Body fermentation enzyme | Trace |

The fermentation is the body is vigorous, and the cells are refreshed frequently and become active.

Embodiment 12

The application of oil products (also can be used for fermentations and nano applications), the composition in percentage by mass is given as follows:

| Bacteria-free water | 30% |
|---|---|
| Carboxyl acid | 10% |
| Fatty acid (Degradated industrial oil) | 20% |
| Calcium sulfate or metal salts | 10% |
| Ammonia water | 10% |
| Carbohydrates (Monosaccharide or Disaccharide) | 20% |
| Special application of fermentation enzyme for oils | Trace |

After the water of the emulsified matter is evaporated or dehydrated, and then melted in various oil products to act as an additive.

Embodiment 13

In the application of producing chemical substances in a plant (used for fermentations and nano applications), the composition in the percentage by mass is given as follows:

| Bacteria-free water | 90% |
|---|---|
| Vinegar or carboxyl acid | 2% |
| Cytokinin-O-glucosides | 2% |
| Calcium sulfate and various inorganic salts (added separately) | 2% |
| Ammonia water | 2% |
| Special DNA, RNA and/or enzyme of a plant | Trace |

A carrier similar to partial cell tissue of a plant or a fatty acid-M-$NH_2$-protein enzyme-sugar carrier together with a solidification carrier (such as R-unhusked rice-$NH_2$-protein enzyme system) is cultivated.

Embodiment 14

In a culture medium used for dividing cells or bacteria or protein enzymes, the composition in percentage by mass:

| Bacteria-free water | 94% |
|---|---|
| Vinegar or carboxyl acid | 2% |
| Hydroxypropylmethyl cellulose (HPMC) | 2% |
| Magnesium sulfate and different inorganic salts (separately added) | 2% |
| Ammonia water | 2% |
| Cell body or bacteria or protein enzyme | Trace |

The cells are purified first.

Embodiment 15

In the application of a nano filtration system (which can be used for fermentation and nano manufacturing, but the maltose cannot be used for nano manufacturing), the composition in percentage by mass is given as follows:

| Bacteria-free water | 92% |
|---|---|
| Vinegar or carboxyl acid | 2% |
| Maltose or other disaccharide | 2% |
| Magnesium sulfate or calcium sulfate | 2% |
| Ammonia water | 2% |
| Fermenter (excluding maltose) | Trace |

A nano filter (film) is produced, and the remaining matter can be observed by a microscope.

Embodiment 16

In a nano solution, the composition in percentage by mass is given as follows:

| Bacteria-free water | 88.89% |
|---|---|
| Vinegar or carboxyl acid | 1.3% |
| Hydroxypropylmethyl cellulose (HPMC) | 1.3% |
| Titanium sulfate | 7.21% |
| Ammonia water | 1.3% |
| Fermenter | Trace |

A nano titanium dioxide particle film is fermented and coated completely and combusted partially, or the titanium dioxide particles are combined with the PVA-SI-M nano inorganic polymer film.

Polyvinyl alcohol (PVA) is organic and silicic acid and M are inorganic, and both are hybridized together to form nano inorganic polymer film, organic and inorganic nano complex body, which are neither organic porous bodies, nor inorganic porous ceramics.

Embodiment 17

In the application of nano ceramics, the composition in percentage by mass is given as follows:

| Bacteria-free water | 86% |
|---|---|
| Venegar or carboxyl acid | 2% |
| Hydroxypropylmethyl cellulose (HPMC) | 2% |
| Titanium sulfate | 10% |
| Ammonia water | 2% |
| Fermenter | Trace |

The foregoing fermented nano solution of metal-polymer cholate(s) is melted and condensed into a gel, and casted into a titanium oxide biscuit, and sintered below 600° C.

Embodiment 18

In the application of nano plastics, the composition in percentage by mass is given as follows:

| | |
|---|---|
| Humic acid | 90 ml |
| Zinc sulfate | 10 g |
| Ammonia water | 0.3% |
| Fermentation by fermenter | |

The foregoing fermented nano solution of metal-polymer chelate(s) 50%

| | |
|---|---|
| Nitrile butadiene rubber (NBR) | 50% |

After the solution is mixed, blended, heated and evaporated gradually, a nano rubber is obtained.

Embodiment 19

In the industrial application of nano textile (also used for fermentations and nano applications), the composition in the percentage by mass:

| | |
|---|---|
| Add bacteria-free water (covered to form a semifluid) | 60% |
| Carboxyl resin- Amberlite IRC-50 | 3% |
| Glucose or monosaccharide | 2% |
| Zinc sulfate or titanium sulfate or aluminum sulfate | 2% |
| Ammonia water (amino resin) | 3% |

The foregoing single hybrid solution and 30% of plant fiber or inorganic polymer powder carrier produce macromolecules of hybrid, and the bacteria are fermented, suspended, and cultivated to obtain a nano scale. It is extruded from plant fibers or inorganic polymer powder carriers and carboxyl resins, and the extruded solution of metal-polymer chelate(s) is disinfected by ultraviolet beams to form R—$NH_2$, which is a nano monosaccharide-M-$NH_2$ (or a nano metal compound) for dyeing and printing.

Embodiment 20

The composition of nano liquid crystals in percentage by mass is given as follows:

| | |
|---|---|
| Bacteria-free water | 92% |
| Venegar or carboxyl acid | 2% |
| Hydroxypropylmethyl cellulose (HPMC) | 2% |
| Silver sulfate | 0.4% |
| Ammonia water | 2% |
| Nucleic acid | Trace |

After the liquid crystal is obtained and completely fermented and coated, a nano liquid crystal conducting film can be obtained by a partial combustion.

Embodiment 21

In the application of organic EL semicondctors (also can be used for fermentations and nano applications), the composition in the percentage by mass:

| | |
|---|---|
| Bacteria-free water | 90% |
| Venegar or carboxyl acid | 2% |
| Glucose or monosaccharide | 2% |
| Iridium sulfate or platinum sulfate | 0.4% |
| Ammonia water | 2% |
| Polymer bridging agent such as PVP | 0.03% |
| Special DNA or RNA (for photosynthesis) | Trace |

Embodiment 22

In the application of biofuel batteries, the composition in percentage by mass is given as follows:

| | |
|---|---|
| Bacteria-free water | 90.6% |
| Vinegar | 1.30% |
| Chitosan powder | 1.30% |
| Copper sulfate | 3.40% |
| Iron sulfate | 3.40% |
| PVP K-30 | 0.01% |

The gene and enzyme fermentation for sprouting alfalfa goes with a ultraviolet coating and a PVA system sensitizer.

Embodiment 23

In the application of a nano inorganic polymer metal hybrid carrier (used for fermentations and nano applications), the composition in the percentage by mass is given as follows:

| | |
|---|---|
| Water | 83% |
| Silicic acid | 3.75% |
| Polyvinyl alcohol | 1.75% |
| Magnesium sulfate or calcium sulfate | 1.5% |

After the thermal decomposition, the soaked carrier is dried slowly and sintered into a ceramic form.

| | |
|---|---|
| Vinegar or carboxyl acid | 2% |
| Chitosan | 2% |
| Bacteria-free water | 96% |
| Fermenter | Trace |

It is fermented automatically and slowly on the whole carrier.

Embodiment 24

In the application of nano inorganic polymer films, hole carriers and sphere materials, the composition in the percentage by mass:

| | |
|---|---|
| Bacteria-free water | 87% |
| Silicic acid | 3.75% |
| Polyvinyl alcohol | 1.75% |
| Vinegar (or carboxyl resin) | 2% |
| Sulfuric acid metal salts or calcium sulfate | 1.5% |
| Glucose or monosaccharide | 2% |
| Ammonia water (amino resin) | 2% |
| Fementer for decomposing sugar | Trace |

In a nano PVA-metal M-$NH_2$-protein enzyme-sugar system, the protein enzyme for decomposing sugar is used, heated, dried and disinfected to form nano inorganic polymer films, hole carriers, sphere materials in PVA-SI-M (which is a nano metal polymer), and another solid-liquid separation method can be used for the same result.

Embodiment 25

In the method and application (for fermentations and nano applications) of a dry protein enzyme (free of water), the composition in percentage by mass is given as follows:

| Bacteria-free water | 94% |
|---|---|
| Vitamin C | 2% |
| Hydroxypropylmethyl cellulose (HPMC) | 2% |
| Iron sulfate or calcium sulfate | 0.4% |
| Ammonia water | 2% |
| Fermenter | Trace |

It is found that the activity of the dry bacteria is still very high, and there will be no time limit.

Embodiment 26

In the method and application (for fermentations and nano applications) of a dry protein enzyme (free of water), the composition in percentage by mass is given as follows:

| Bacteria-free water | 94% |
|---|---|
| Vitamin C | 2% |
| Chitosan | 2% |
| Iron sulfate or calcium sulfate | 0.4% |
| Ammonia water | 2% |
| Fermenter | Trace |

It is found that the activity of dry bacteria is still very high and thus there will be no time limit.

Embodiment 27

In the application of biochips (free of water), the composition in percentage by mass is given as follows:

| Bacteria-free water | 94% |
|---|---|
| Vitamin C | 2% |
| Glucose or monosaccharide | 2% |
| Iron sulfate | 0.4% |
| Ammonia water | 2% |
| DNA | Trace |

A plant fiber is used as a carrier for the fermentation.

It is extruded from the plant fiber and printed onto a nano inorganic polymer film to act as a carrier chip and a polymer hybrid R.

Embodiment 28

In the application of biochips (free of water), the composition in percentage by mass is given as follows:

| Add bacteria-free water (covered to form a fluid) | 80% |
|---|---|
| Vitamin C | 2% |
| Hydroxypropylmethyl cellulose (HPMC) | 2% |
| Iron sulfate or calcium sulfate | 0.4% |
| Polylysine or aminosilane 16% | |
| (after being dried and solified into powder) | |
| Fermentation biological protein | Trace |

After going through the cultivation and fermentation and solid-liquid separation, the solution (already having no amino enzyme and unable to be preserved for long) is "grafted" according to the foregoing method on a chip carrier of an amino resin or inorganic matter such as polylysine or aminosilane.

Embodiment 29

In the application of an artificial imitated glucosamine, the composition in percentage by mass is given as follows:

| Carboxyl resin | 3% |
|---|---|
| Water | 91% |
| Glucose | 3% |
| Calcium sulfate | 0.01% |
| Ammonia water or urea | 3% |

A plant fiber is used as a carrier to promote the reaction and extruded from the fiber to form glucose-trace of calcium-$NH_2$ (an amino metal compound that can be used for dietic health care s, cosmetics, and emulsification functions. If a coconut fiber and/or palm fiber (containing fatty acid or carboxyl acid fiber) is used as a carrier that uses urea for the reaction, and the carrier is extruded from the fibers to form a quaternary ammonium cation liquid that can be used for baby shampoo and disinfection functions.

Embodiment 30

In the application of a biological cell or bacteria or protein enzyme cultivation purification, the composition in percentage by mass is given as follows:

| Add bacteria-free water (covered to form a semifluid) | 60% |
|---|---|
| Grinded unhusked rice (glycan matter and calcium) | 7% |
| (Such nano metal polymer can be imitated artificially) | |
| Ammonia water | 3% |
| Fermentation bacteria | Trace |

Minced plant fibers (including carboxyl acid fibers) 30% or carboxyl resins such as amberlite IRC-50 are used. If a carrier is suspended and cultivated for a fermentation to promote the reaction and form R-unhusked rice-$NH_2$-protein enzyme to be filtered and extracted from the fiber or carboxyl resin to produce a purified biological cell or bacteria or protein enzyme.

Embodiment 31

In the application of a biological cell or bacteria or protein enzyme cultivation purification, the composition in percentage by mass is given as follows:

| Killed bacteria passing through peat | 5% |
|---|---|
| Calcium sulfate | 2% |
| (Add a trace of bacteria-free water.) | |

The foregoing two are mixed, permeated evenly and solidified, and then the sulfuric acid radicals are backed and blown away to form:

| Peat-calcium | |
|---|---|
| Bacteria-free water | 90% |
| Ammonia water | 3% |
| Fermentation bacteria | Trace |

Minced plant fibers (including carboxyl acid fibers) are used, such that the carrier or not used as a carrier is suspended and cultivated for the fermentation to promote the reaction and form a R-peat-calcium-$NH_2$-protein enzyme which is filtered and extracted from the fiber and peat (including calcium and amino bridge therein to form an amino nano metal polymer) to produce a purified biological cell or bacteria or protein enzyme is produced.

Embodiment 32

In the application of a biological cell or bacteria or protein enzyme cultivation purification, the composition in percentage by mass is given as follows:

| | |
|---|---|
| Vinegar | 2% |
| Chitosan (The higher CPS, the better) | 4% |
| Calcium sulfate | 3% |
| Bacteria-free water | 92% |

The foregoing two are mixed evenly and precipitated after going through an pH-balanced precipitation and the solid calcium hybrid is filtered (such that it no longer contains any acetic acid), and the sulfuric acid radicals are dried and blown away to produce.

| | |
|---|---|
| Chitosan-calcium | |
| Add bacteria-free water (covered to form a semifluid) | 20% |
| Ammonia water | Trace |
| Fermented bacteria | Trace |

A carboxyl resin such as amberlite IRC-50 of approximately 4% or minced plant fibers (including carboxyl acid fibers) is used. After the carrier is suspended and cultivated for the fermentation to form R-chitosan and calcium-$NH_2$-protein enzyme and the fiber and chitosan (including calcium and amino bridges therein) is filtered and extracted, purified biological cell or bacteria or protein enzyme is produced.

While the invention has been described in terms of what is presently considered to be the most practical and preferred embodiments, it is to be understood that the invention is not limited to the disclosed embodiment. On the contrary, it is intended to cover various modifications and similar arrangements included within the spirit and scope of the appended claims which are to be accorded with the broadest interpretation so as to encompass all such modifications and similar structures.

INDUSTRIAL APPLICATION

The present invention provides a hybrid structured polymer, wherein the concentration of an acidic hydroxypropylmethyl cellulose (HPMC) solution is equal to 0.1~10%, which is in fact produced by water:acetic acid or other acids: hydroxypropylmethyl cellulose (HPMC) or other (chemical substance-OH)$_n$ polymer:acidic or monovalent, bivalent, or trivalent metal chloride ions in the proportion of 97:1:1:1 and 88:4:4:4 and blended sequentially with each other, and ammonia (or amine matter) already has amino groups, and thus the bacteria or enzyme or smaller nucleic acid or some cell body can be fermented and growed for producing biochemical and nano liquid crystal materials.

Compared with the prior art, the foregoing technical solution of the present invention has the following advantages:

1. The invention provides a quick reaction for the solvent gas or liquid, without requiring high temperature and high pressure, and the reaction can be performed at room temperature and thus the invention is cost effective and capable of saving a great deal of financial resources and material resources.

2. The invention is very safe and free of worrying about the industrial safety, since it does not require any fire or combustion.

3. The invention provides long expiration time, worn-out resistance and life expectancy, and it is free from saturation due to the catalysis.

4. The invention solves the problem of organic solvent treatment and the difficulty of fermentation, and also overcome the bottlenecks on the oxidation capability, condensation capability, oxidizing condensation capability, and degradation capability of the reaction.

5. The invention creates an artificial imitated chitosan solution containing metal ions to improve the sources and diversified applications of chitosan.

6. The invention creates a new culture medium for gas detection, artificial imitated glucosamine, disinfectant, biochemical reaction for fermentations, biological protein and its metabolite purification, genetic engineering, bacteria preservation system, medical science, oil product, plant, semiconductor applicability and cell multiplication.

7. The invention creates a new technology for producing nano filtrations, nano materials, nano ceramics, nano plastics and nano textiles.

8. The invention provides a very good metal enzyme biocatalyst.

9. The invention creases a new technology for producing batteries, liquid crystal materials and biochips.

What is claimed is:

1. A solution of solidified metal-polymer chelates comprising:
   0.1-99.87 percent by weight water;
   0.1-40 percent by weight of a carboxyl acid;
   0.1 to 30 percent by weight of hydroxyl functional carbohydrate polymer;
   0.1 to 30 percent by weight of a metal salt;
   amino compounds; and
   trace amounts of biological proteins, wherein the amino compounds, carbohydrate polymer, metal and proteins form an amino polymer metal protein hybrid, where the metal ion acts as a bridge between the hydroxyl groups of the carbohydrate polymer and the amino compounds.

2. The solution of metal-polymer chelates of claim 1, the biological proteins being dissolved with an electric potential suitable for the biological protein.

3. The solution of metal-polymer chelates of claim 1, further comprising carbohydrate molecules having at least one nonsaccharide bimolecule of monosaccharide derivatives.

4. The solution of metal-polymer chelates of claim 1, further comprising:
   at least one alkali.

5. The solution of metal-polymer chelates of claim 1, wherein the metal salts are selected from a group consisting of beryllium, magnesium, calcium, strontium, barium, radium, nickel, chromium, lead, copper, iron, zinc, titanium, manganese, cobalt, silver, gold, platinum, palladium, cadmium, lithium, rubidium, cesium, mercury, tin, zirconium, aluminum, thallium, antimony, bismuth, germanium, gallium, molybdenum, tungsten, yttrium, scandium, rhodium, iridium, technetium, osmium, ruthenium, rhenium, vanadium, and indium.

6. The solution of metal-polymer chelates of claim 1, wherein the carboxylic acid is selected from a group consisting of monocarboxylic acid, dicarboxylic acid, tricarboxylic acid, acetic acid, L-ascorbate, 2-hydroxybenzoic acid, methanoic acid, propionic acid, propanedioic acid, 2-hydroxypropanoic acid, hydroxybutanedioic acid, butanedioic acid, hexanedioic acid, cis-butendioic acid, trans-butendioic acid, ethanedioic acid, dodecanoic acid, 2,3-dihydrobutanedioic acid, humic acid, nitrified humic acid, fatty acid, opines in a plant, carboxyl acid fiber, and carboxyl resin.

7. The solution of metal-polymer chelates of claim 1, further comprising a hydroxyl-containing compound selected from a group consisting of sucrose, maltose, lactose, trehalose, chitosan, degraded oils, seaweed cell wall, unhusked rice, cytokinin-O-glucosides, amino group containing polyvinyl alcohol, polyvinyl alcohol, humic acid, nitrified humic acid, peat, hydroxypropylmethyl cellulose, and a mixture of oil and sugar.

8. The solution of metal-polymer chelates of claim 1, further comprising bacteria or cells containing biological proteins selected from a group consisting of a protein enzyme, and a protein.

9. The solution of metal-polymer chelates of claim 1, further comprising a silicic acid bearing molecule.

10. The solution of metal-polymer chelates of claim 1, further comprising:
a clay.

11. The solution of metal-polymer chelates of claim 1, further comprising a plastic polymer.

12. The solution of metal-polymer chelates of claim 1, in which the solution is capable of being used in an oxidation process so as to produce oxygen anions.

13. The solution of metal-polymer chelates of claim 1, in which the solution is capable of being used for a condensation having at least one oxidizing condensation.

14. The solution of metal-polymer chelates of claim 1, in which the solution is capable of being used in one of a hydroxypropylmethyl cellulose mimic of chitosan and a monosaccharide mimic of glucosamine.

15. The solution of metal-polymer chelates of claim 1, in which the solution is capable of being used in the cultivation and purification of the biological protein bearing biological molecules and their metabolites.

16. The solution of metal-polymer chelates of claim 1, in which the solution is capable of being used in a metal enzyme biocatalyst.

17. The solution of metal-polymer chelates of claim 1, in which the solution is capable of being used in a disinfectant.

18. The solution of metal-polymer chelates of claim 1, in which the solution is capable of being used in a biological protein bearing biological molecules culture medium preservation system.

19. The solution of metal-polymer chelates of claim 1, in which the solution is capable of being used for dietary treatments and for health care applications.

20. The solution of metal-polymer chelates of claim 1, in which the solution is capable of being used for the production of chemical components of a plant.

21. The solution of metal-polymer chelates of claim 1, in which the solution is capable of being used for duplication of genes and carriers.

22. The solution of metal-polymer chelates of claim 1, in which the solution is capable of being used in a nano filtration system.

23. The solution of metal-polymer chelates of claim 1, in which the solution is capable of being used for the production of a nano material.

24. The solution of metal-polymer chelates of claim 1, in which the solution is capable of being used for one of the nano inorganic matter, nano ceramic, nano plastic and nano textile industries.

25. The solution of metal-polymer chelates of claim 1, in which the solution is capable of being used in one of the manufacture of biological liquid crystals, biological semiconductors and biochips.

26. The solution of metal-polymer chelates of claim 1, in which the solution is capable of being used for biological batteries.

27. The solution of metal-polymer chelates of claim 1, in which the solution is capable of being used for processing an oil product.

28. The solution of metal-polymer chelates of claim 1, the metal-polymer chelates mixed with a compound being selected from a group consisting of: polymer bridging agent, inorganic polymer carrier, inorganic and organic bridge polymer, nano inorganic polymer, plant fiber, carboxyl acid fiber, modification having carboxyl acid fiber, carboxyl resin, amino resin, and inorganic matter.

29. The solution of metal-polymer chelates of claim 1, wherein the solution of metal-polymer chelates further comprising a moisture absorbent combined with the metal-polymer chelates.

30. The solution of metal-polymer chelates of claim 28, the polymer bridging agent comprising polyvinylpyrrolidone.

31. The solution of metal-polymer chelates of claim 28, wherein the metal-polymer chelates is capable of producing at least one substance, the substance being selected from the group consisting of: amino metal compound, an amino metal polymer, an amino nano metal polymer, an amino nano metal compound, a nano metal polymer, a nano metal compound, an amino biological protein bearing biological molecules, and a pure biological protein bearing biological molecules.

* * * * *